(12) United States Patent
Cohen et al.

(10) Patent No.: US 11,783,940 B2
(45) Date of Patent: Oct. 10, 2023

(54) AUGMENTED REALITY-BASED TRAINING AND TROUBLESHOOTING FOR MEDICAL DEVICES

(71) Applicant: Fresenius Medical Care Holdings, Inc., Waltham, MA (US)

(72) Inventors: Harvey Cohen, Newton, MA (US); Matthew Buraczenski, Holden, MA (US); John E. Tremblay, Bolton, MA (US); Kulwinder S. Plahey, Martinez, CA (US); Stephen A. Merchant, Sudbury, MA (US); James Peterson, Benicia, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 146 days.

(21) Appl. No.: 17/245,135

(22) Filed: Apr. 30, 2021

(65) Prior Publication Data
US 2021/0249129 A1 Aug. 12, 2021

Related U.S. Application Data

(62) Division of application No. 16/258,020, filed on Jan. 25, 2019, now Pat. No. 11,031,128.

(51) Int. Cl.
*G16H 40/63* (2018.01)
*G16H 30/40* (2018.01)
(Continued)

(52) U.S. Cl.
CPC ............. *G16H 40/63* (2018.01); *G06V 20/20* (2022.01); *G16H 30/40* (2018.01); *G06F 3/016* (2013.01); *G06F 3/167* (2013.01); *H04N 7/15* (2013.01)

(58) Field of Classification Search
CPC ........ G16H 40/63; G16H 30/40; G16H 40/60; G06V 20/20; G06F 3/016; G06F 3/167; H04N 7/15
See application file for complete search history.

(56) References Cited

U.S. PATENT DOCUMENTS 7,857,756 B2 12/2010 Warren et al.
8,043,224 B2 10/2011 Sarel
(Continued)

FOREIGN PATENT DOCUMENTS

WO 2013/170204 A1 11/2013
WO 2017/015393 A1 1/2017
(Continued)

OTHER PUBLICATIONS

PCT International Search Report and Written Opinion in Application No. PCT/US2020/012479, dated Jun. 23, 2020, 18 pages.
(Continued)

*Primary Examiner* — Santiago Garcia
(74) *Attorney, Agent, or Firm* — Fish & Richardson P.C.

(57) ABSTRACT

Augmented reality-based training and troubleshooting is described for medical devices. An electronic mobile device can be equipped with an AR application that, when executed, causes the electronic mobile device to provide augmented reality-based training on how to set up, or perform maintenance on, one or more components of a medical device. The AR application, when executed, can also cause the electronic mobile device to provide augmented reality-based troubleshooting for one or more components of a medical device.

21 Claims, 11 Drawing Sheets

(51) Int. Cl.
    *G06V 20/20*     (2022.01)
    *G06F 3/01*     (2006.01)
    *G06F 3/16*     (2006.01)
    *H04N 7/15*     (2006.01)

(56) References Cited

U.S. PATENT DOCUMENTS

| | | |
|---|---|---|
| 8,606,595 B2 | 12/2013 | Udani |
| 8,655,796 B2 | 2/2014 | Udani |
| 8,690,155 B2 | 4/2014 | Riley |
| 8,848,974 B2 | 9/2014 | Qureshi et al. |
| 9,042,596 B2 | 5/2015 | Connor |
| 9,224,180 B2 | 12/2015 | Macoviak et al. |
| 9,344,612 B2 | 5/2016 | Ritchey et al. |
| 9,427,305 B2 | 8/2016 | Kuraguntla et al. |
| 9,610,476 B1 | 4/2017 | Tran et al. |
| 9,697,556 B2 | 7/2017 | Mazed et al. |
| 9,727,042 B2 | 8/2017 | Hoffberg-Borghesani et al. |
| 9,805,624 B2 | 10/2017 | Reihsen et al. |
| 9,826,903 B2 | 11/2017 | Derchak |
| 9,832,412 B2 | 11/2017 | Burkholz et al. |
| 9,907,730 B2 | 3/2018 | Macoviak et al. |
| 9,924,905 B2 | 3/2018 | Kuraguntla et al. |
| 9,936,906 B2 | 4/2018 | Satish et al. |
| 9,971,894 B2 | 5/2018 | Shear et al. |
| 10,003,945 B2 | 6/2018 | Papakonstantinou et al. |
| 10,010,379 B1 | 7/2018 | Gibby et al. |
| 2006/0072797 A1 | 4/2006 | Weiner et al. |
| 2007/0191070 A1 | 8/2007 | Rao |
| 2009/0265188 A1 | 10/2009 | Lamy et al. |
| 2009/0281838 A1 | 11/2009 | Lynn et al. |
| 2009/0299645 A1 | 12/2009 | Colby et al. |
| 2010/0080415 A1 | 4/2010 | Qureshi et al. |
| 2011/0307079 A1 | 12/2011 | Oweiss et al. |
| 2012/0138533 A1 | 6/2012 | Curtis et al. |
| 2012/0323590 A1 | 12/2012 | Udani |
| 2012/0323805 A1 | 12/2012 | Udani |
| 2013/0117040 A1 | 5/2013 | James et al. |
| 2013/0177222 A1 | 7/2013 | Tridandapani et al. |
| 2013/0182930 A1 | 7/2013 | Trzasko et al. |
| 2013/0301901 A1 | 11/2013 | Satish et al. |
| 2014/0216250 A1* | 8/2014 | Meyer ............... A61M 1/3627 95/1 |
| 2014/0217020 A1* | 8/2014 | Meyer ............... A61M 1/1696 96/182 |
| 2014/0217029 A1* | 8/2014 | Meyer ............... A61M 1/1656 210/647 |
| 2014/0243614 A1 | 8/2014 | Rothberg et al. |
| 2014/0243652 A1 | 8/2014 | Pashko |
| 2014/0266983 A1 | 9/2014 | Christensen |
| 2014/0295392 A1 | 10/2014 | Rock |
| 2015/0046818 A1 | 2/2015 | Wade |
| 2015/0154751 A1 | 6/2015 | Satish et al. |
| 2015/0173715 A1 | 6/2015 | Raghavan et al. |
| 2015/0320357 A1 | 11/2015 | Kuraguntla et al. |
| 2015/0335288 A1 | 11/2015 | Toth et al. |
| 2016/0012538 A1 | 1/2016 | Costaceque-Cecchi-Dimeglio et al. |
| 2016/0015470 A1 | 1/2016 | Border |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0019715 A1 | 1/2016 | Haddick et al. |
| 2016/0019719 A1 | 1/2016 | Osterhout et al. |
| 2016/0021304 A1 | 1/2016 | Osterhout |
| 2016/0071325 A1 | 3/2016 | Callaghan |
| 2016/0125765 A1* | 5/2016 | Meretei ............... G09B 23/28 434/262 |
| 2016/0228640 A1 | 8/2016 | Pindado et al. |
| 2016/0375592 A1 | 12/2016 | Szatmary et al. |
| 2017/0017083 A1 | 1/2017 | Samec et al. |
| 2017/0039423 A1 | 2/2017 | Cork et al. |
| 2017/0043257 A1 | 2/2017 | Kraly et al. |
| 2017/0173262 A1 | 6/2017 | Veltz |
| 2017/0181629 A1 | 6/2017 | Mahalingam et al. |
| 2017/0212769 A1 | 7/2017 | Yang |
| 2017/0229044 A1 | 8/2017 | Benson et al. |
| 2017/0323481 A1 | 11/2017 | Tran et al. |
| 2017/0325733 A1 | 11/2017 | Hettrick et al. |
| 2017/0337438 A1 | 11/2017 | El et al. |
| 2018/0036884 A1 | 2/2018 | Chen et al. |
| 2018/0092698 A1 | 4/2018 | Chopra et al. |
| 2018/0116723 A1 | 5/2018 | Hettrick et al. |
| 2018/0125419 A1 | 5/2018 | Yun et al. |
| 2018/0211730 A1 | 7/2018 | Slepian et al. |
| 2018/0220931 A1 | 8/2018 | Salamini et al. |
| 2018/0225993 A1 | 8/2018 | Buras et al. |
| 2018/0242920 A1 | 8/2018 | Hresko et al. |
| 2019/0254754 A1 | 8/2019 | Johnson et al. |
| 2020/0202134 A1 | 6/2020 | Bulzacki et al. |
| 2020/0211679 A1 | 7/2020 | Pellini et al. |
| 2020/0243193 A1 | 7/2020 | Plahey et al. |
| 2020/0342228 A1* | 10/2020 | Prevrhal ............... G06V 20/20 |
| 2020/0387127 A1* | 12/2020 | McGill ............... G05B 19/0423 |
| 2021/0327303 A1* | 10/2021 | Buras ............... A61B 8/085 |
| 2022/0027629 A1* | 1/2022 | Case ............... G02B 27/0172 |
| 2022/0188545 A1* | 6/2022 | Nagar ............... G06F 3/017 |

FOREIGN PATENT DOCUMENTS

| | | |
|---|---|---|
| WO | 2017/066340 A1 | 4/2017 |
| WO | 2017/160920 A1 | 9/2017 |
| WO | 2018/013411 A1 | 1/2018 |
| WO | 2018/013413 A1 | 1/2018 |
| WO | 2018/013414 A1 | 1/2018 |
| WO | 2018/013417 A1 | 1/2018 |
| WO | 2018/022523 A1 | 2/2018 |
| WO | 2018/049250 A1 | 3/2018 |
| WO | 2018/094479 A2 | 5/2018 |

OTHER PUBLICATIONS

Zgoura et al., "Virtual reality simulation in peritoneal dialysis training: the beginning of a new era", Blood Purif, pp. 1-5, Dec. 2018.

International Preliminary Report on Patentability in International Appln. No. PCT/US2020/012479, dated Aug. 5, 2021, 14 pages.

\* cited by examiner

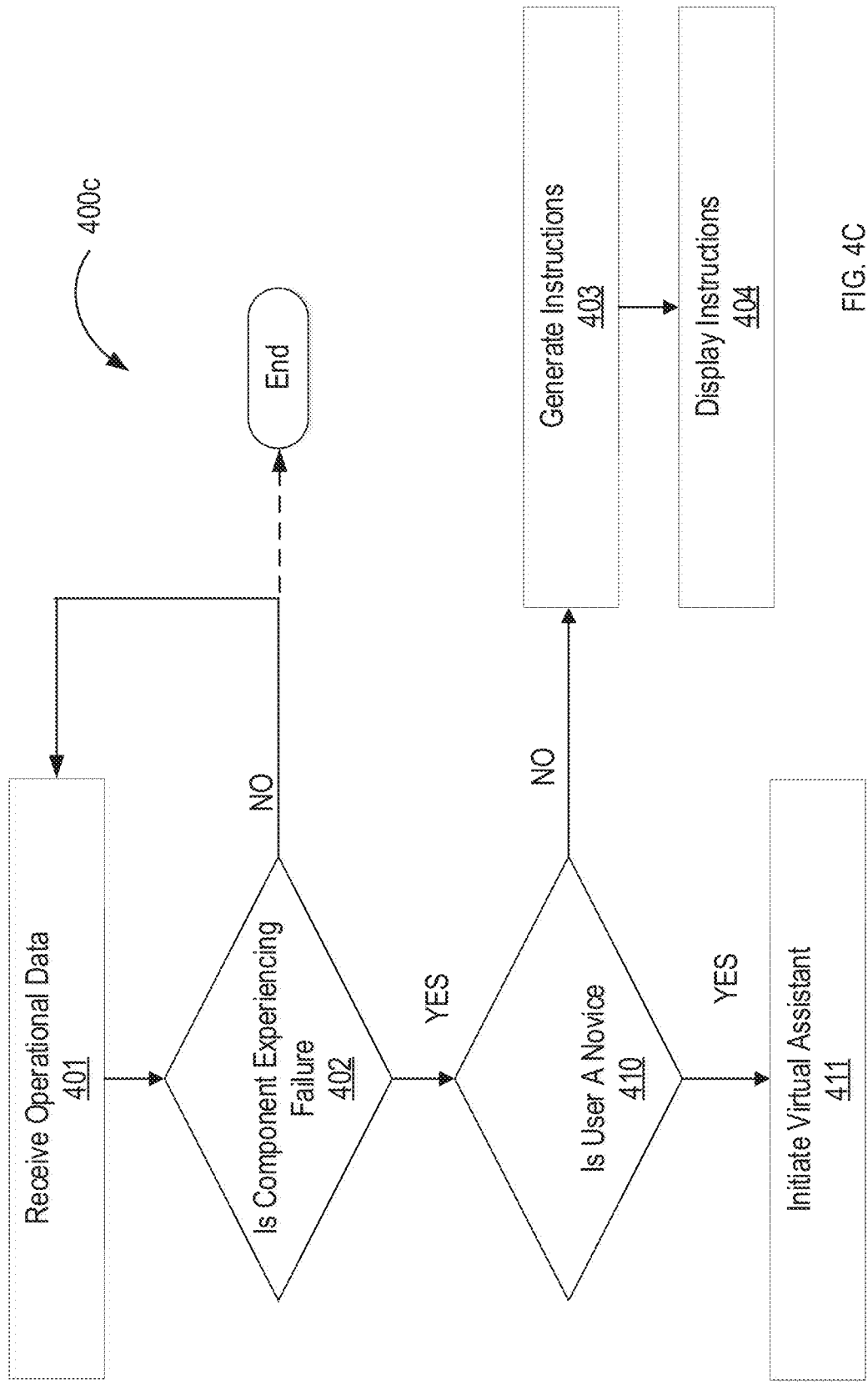

AUGMENTED REALITY-BASED TRAINING AND TROUBLESHOOTING FOR MEDICAL DEVICES

CROSS-REFERENCE TO RELATED APPLICATIONS

This application is a divisional application of and claims priority to U.S. application Ser. No. 16/258,020, filed on Jan. 25, 2019.

FIELD OF THE INVENTION

This disclosure generally relates to systems and methods that provide training for the setup, maintenance, and troubleshooting of medical devices. In particular, this description generally relates to systems and methods that provide augmented-reality based training for the setup, maintenance, and troubleshooting of medical devices.

BACKGROUND

Medical devices, such as dialysis machines, can be complex and may require users (e.g., health care professionals and/or patients) to understand information about storage, use, disposal, and/or reprocessing of various components. Typically, manufacturers of medical devices supply instructions-for-use (IFU) with their medical devices that generally provide, among other things, instructions on how to set up and troubleshoot the various components of the medical devices. Design considerations of the instructions-for-use may be important if a medical device requires complex actions, has confusing setup procedures, or has the potential to harm a user of the medical device. Design considerations for instructions-for-use have traditionally focused on textual content and layout. Furthermore, it has become increasingly popular to design medical devices for home use. Approaches to designing medical devices for home use typically involve simplifying the device's machinery such that it is easier for a patient lacking technical skills to operate the devices. However, even though devices can be simplified for home use, the devices may still require training and instructions to ensure that the device is configured for safe operations.

SUMMARY

In at least one aspect of the present disclosure, a system is provided. The system includes a medical device having one or more tags. Each tag of the one or more tags are associated with a component of the medical device. The system includes an electronic mobile device. The electronic mobile device includes a computer-readable medium configured to store information corresponding to the component associated with each tag, the information including one or more user-executable instructions associated with the component, the computer-readable medium including computer-executable instructions. The computer-executable instructions include an operating system and an augmented reality application configured to be executed by the operating system. The electronic mobile device includes one or more processors configured to execute the computer-executable instructions, a user interface configured to be communicatively coupled to the one or more processors, and one or more sensors configured to be communicatively coupled to the one or more processors and further configured to capture image data. When the operating system is executing the augmented reality application, the one or more processors carry out operations to: cause the one or more sensors to begin capturing image data; determine if the image data includes at least one of the one or more tags; if the image data includes at least one of the one or more tags, determine a component of the medical device associated with the at least one tag; retrieve, from the computer-readable medium, the information associated with the component of the medical device associated with the at least one tag; and cause the user interface to display one or more indicators corresponding to the information associated with the component, the one or more indicators including one or more of a static image, an animated image, or both.

When the operating system is executing the augmented reality application, the one or more indicators corresponding to the information associated with the component can include one or more of a first indicator indicating that the component is correctly set up or operating correctly or a second indicator indicating that the component is incorrectly set up or operating incorrectly. The second indicator can include information to indicate a process to correct setup of the component or to modify incorrect operation of the component.

When the operating system is executing the augmented reality application, the one or more processors can further carry out operations to cause the user interface to prompt the user to carry out the user-executable instructions included in the information corresponding to the component of the medical device associated with the at least one tag. The user executable instructions can include at least one of: instructions related to setting-up the component of the medical device, instructions related to performing maintenance on the component of the medical device, and instructions related to troubleshooting the component of the medical device.

When the operating system is executing the augmented reality application, the one or more processors can further carry out operations to: cause the one or more sensors to capture image data associated with the user performing the user-executable instructions, generate feedback based on the data associated with the user performing the user-executable instructions, and cause the user interface to display the feedback to the user. The generated feedback can correspond to whether or not the user performed the user-executable instructions correctly.

The augmented reality application can include a novice mode. The one or more processors can be further configured to be communicatively coupled with a controller circuit of the medical device. When the operating system is executing the augmented reality application in novice mode, the one or more processors can further carry out operations to send an idle control signal to the controller circuit of the medical device, where in response to receiving the idle control signal, the controller circuit can cause the medical device to operate in an idle mode, cause the sensor to capture image data associated with the user performing the user-executable instructions, determine, based on the image data associated with the user performing the user-executable instructions, whether or not the medical device is properly configured to perform medical operations, and send an operate control signal to the controller circuit of the medical device if the one or more processors determine that the medical device is properly configured to perform medical operations, wherein in response to receiving the operate control signal the controller circuit causes the medical device to operate in a functional mode. The medical device can be disabled from performing medical operations when the device is operating in idle mode and the medical device is able to perform medical operations when the device is operating in functional mode.

The medical device can be a dialysis machine.

The system can include a remotely located database configured to store historical data associated with at least one of: the medical device or at least one remote device that is substantially similar to the medical device. When the operating system is executing the augmented reality application, the one or more processors can further carry out operations to receive the historical data. The retrieved information associated with the component of the medical device associated with the at least one tag can be based at least partially on the received historical data.

In at least one other aspect of the present disclosure, a method is provided. The method includes causing one or more sensors to capture image data, determining if the image data includes at least one of one or more tags, wherein each of the one or more tags is associated with a component of a medical device, if the image data includes the at least one tag, determine a component of the medical device associated with the at least one tag, retrieving information associated with the component of the medical device associated with the at least one tag, wherein the information includes one or more user-executable instructions associated with the component; and displaying one or more indicators corresponding to the information associated with the component of the medical device associated with the at least one tag, the one or more indicators including one or more of a static image, an animated image, or both.

The method can further include prompting a patient who is the subject of healthcare to carry out the user-executable instructions included in the information corresponding to the component of the medical device, wherein the user-executable instructions comprise at least one of: instructions related to setting-up the component of the medical device, instructions related to performing maintenance on the component of the medical device, and instructions related to troubleshooting the component of the medical device. The method can further include causing the one or more sensors to capture image data associated with the patient performing the user-executable instructions; generating feedback based on the data associated with the user performing the user-executable instructions; and displaying the feedback to the patient. The method can further include causing the medical device to operate in idle mode, causing the one or more sensors to capture image data associated with the patient performing the user-executable instructions, determining, based on the image data associated with the patient performing the user executable instructions, whether or not the medical device is properly configured to perform medical operations, and causing the medical device to operate in a functional mode if it is determined that the medical device is properly configured to perform medical operations.

The generated feedback can inform the patient whether or not the patient performed the user-executable instructions correctly. Causing the medical device to operate in idle mode can include disabling the medical devices ability to perform medical operations and causing the medical device to operate in functional mode can include enabling the medical device to perform medical operations.

In at least one other aspect of the present disclosure, a system is provided. The system includes a medical device. The medical device includes one or more components, each component of the one or more components having one or more operational parameters; and one or more monitoring devices configured to detect the one or more operational parameters of at least one component of the one or more components. The system includes an electronic mobile device. The electronic mobile device includes a computer-readable medium having computer-executable instructions, the computer-executable instructions including an operating system, and an augmented reality application configured to be executed by the operating system. The electronic mobile device includes one or more processors configured to: execute the computer-executable instructions, be communicatively coupled to the one or more monitoring devices, and receive operational data associated with the one or more operational parameters of the at least one component. The electronic mobile device includes a user interface communicatively coupled to the one or more processors. When the operating system is executing the augmented reality application, the one or more processors are configured to carry out operations to: receive the operational data associated with the one or more operational parameters of the at least one component; determine if the at least one component is experiencing an at least partial failure based on the operational data; generate one or more user-executable instructions based on the determining if the at least one component is experiencing an at least partial failure; and cause the user interface to display the user-executable instructions.

The user-executable instructions can include information on how to confirm that the at least one component is experiencing the at least partial failure. When the operating system is executing the augmented reality application, the one or more processors can further carry out operations to cause the user interface to prompt the user to confirm the at least partial failure. The user-executable instructions can include information relating to how to fix the at least partial failure.

When the operating system is executing the augmented reality application, the one or more processors can further carry out operations to: generate a confidence value for the determination that the at least one component is experiencing the at least partial failure; cause the user interface to prompt the user to confirm the at least partial failure if the confidence value is greater than a first confidence value threshold and lesser than a second confidence value threshold; and cause the user interface to prompt the user to fix the at least partial failure if the confidence value is greater than the second confidence value threshold.

The one or more processors can include at least one machine learning algorithm that determines if the at least one component is experiencing the at least partial failure and generates the one or more user-executable instructions. The electronic mobile device can be configured to initiate a real-time video conference with an expert technician based on the magnitude of the at least partial failure.

When the operating system is executing the augmented reality application, the one or more processors can further carry out operations to prompt the user to confirm one of a plurality of user experience levels and the electronic mobile device is configured to initiate a real-time video conference with an expert technician based on the user confirmed user experience level.

The system can further include a remotely located database configured to store historical data associated with at least one of: the medical device or at least one remote device that is substantially similar to the medical device. When the operating system is executing the augmented reality application, the one or more processors can further carry out operations to receive the historical data. Determining if the at least one component is experiencing an at least partial failure can be based at least partially on the received historical data.

In at least one other aspect of the present disclosure, a method is provided. The method includes receiving operational data associated with one or more operational parameters of at least one component of a medical device, determining if the at least one component is experiencing an at least partial failure based on the operational data, generating one or more user executable instructions based on the determining if the at least one component is experiencing an at least partial failure, and displaying the one or more user executable instructions.

The user executable instructions can include information on how to confirm that the at least one component is experiencing the at least partial failure, the method further comprising prompting a patient to confirm the at least partial failure. The user-executable instructions can include information relating to how to fix the at least partial failure.

The method can include generating a confidence value for the determination that the at least one component is experiencing an at least partial failure, prompting a patient to confirm the at least partial failure if the confidence value is greater than a first confidence value threshold and below a second confidence value threshold, and prompting the user to fix the at least partial failure if the confidence value is greater than the second confidence value threshold. The method can include initiating a real-time video conference with an expert technician based on the magnitude of the at least partial failure. The method can include prompting a patient to confirm one of a plurality of user experience levels initiating a real-time video conference with an expert technician based on the user confirmed user experience level.

In at least one other aspect of the present disclosure, a system is provided. The system includes a medical device. The medical device includes one or more components, each component of the one or more components having one or more operational parameters; and one or more displays configured to display one or more numerical values associated with the one or more operational parameters of at least one component of the one or more components. The system includes an electronic mobile device. The electronic mobile device includes a computer-readable medium comprising computer-executable instructions. The computer-executable instructions includes an operating system, and an augmented reality application configured to be executed by the operating system. The electronic mobile device includes one or more processors configured to execute the computer-readable instructions, a user interface configured to be communicatively coupled to the one or more processors, and one or more sensors configured to be communicatively coupled to the one or more processors and further configured to capture image data. When the operating system is executing the augmented reality application, the one or more processors carry out operations to: cause the one or more sensors to begin detecting the one or more numerical values associated with one or more operational parameters, wherein the one or more sensors are configured to further detect changes associated with the one or more numerical values, and cause the user interface to display an illustrative representation associated with the detected one or more numerical values.

The one or more displays can include one or more LED displays. The illustrative representation can include a dial display. The illustrative representation can include a meter display. When the operating system is executing the augmented reality application, the one or more processors can further carry out operations to generate a graph in real time, the graph representing trend data associated with the detected one or more numerical values. When the operating system is executing the augmented reality application, the one or more processors can further carry out operations to compare the trend data against threshold values and determine if the at least one component is experiencing an at least partial failure. When the operating system is executing the augmented reality application, the one or more processors can further carry out operations to alert the patient when it is determined that at least one component is experiencing an at least partial failure. The alert can include the one or more processors causing the electronic mobile device to at least one of vibrate or generate an audible sound.

These and other aspects, features, and implementations can be expressed as methods, apparatus, systems, components, program products, means or steps for performing a function, and in other ways.

These and other aspects, features, and implementations will become apparent from the following descriptions, including the claims.

BRIEF DESCRIPTION OF THE DRAWINGS

FIG. 4C shows a flowchart depicting an example of a method for providing virtual assistance for augmented reality-based troubleshooting for medical devices, in accordance with one or more embodiments of the present disclosure.

DETAILED DESCRIPTION

Figure 1:
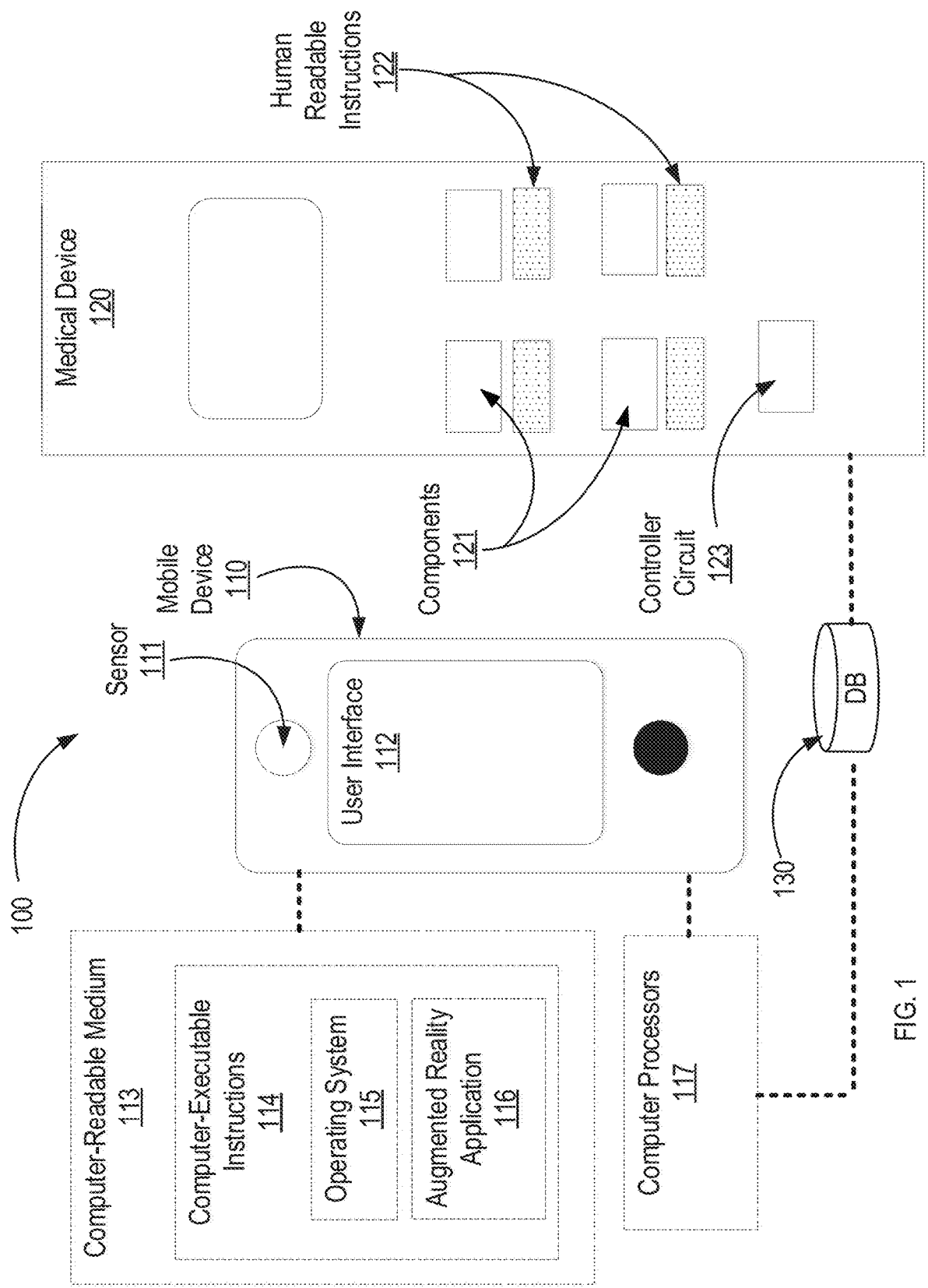
FIG. 1 shows an example of a system for providing augmented reality-based training for medical devices, in accordance with one or more embodiments of the present disclosure.

Existing IFU designs tend to be static and paper-based, which may limit the effectiveness of training and device troubleshooting. These traditional IFUs can limit the effectiveness in many ways, particularly, for example, in connection with difficult user experiences during complex training on the medical devices. These difficult training experiences may contribute to lower therapy adoption and retention rates, especially in the case of home users. Furthermore, even with more simplified designs, many medical devices may still require IFUs for user guidance.

Augmented reality (AR) technology allows overlay of computer-generated graphics on a person's view of the real world. AR technology can be an effective tool to provide a dynamic, user-friendly, and interactive approach to training. Thus, it may be desirable to provide AR-based systems for training people to use and troubleshoot medical devices, such that the overall training experience is improved. This improvement in training experience may contribute to higher therapy adoption and retention rates.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships, or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings are provided, data related to a particular heading, but not found in the section having that heading, may also be found elsewhere in this description.

FIG. 1 shows an example of a system 100 for providing augmented reality-based training for medical devices, in accordance with one or more embodiments of the present disclosure. The system 100 includes a mobile device 110, a medical device 120, and a remotely located database 130. The mobile device 110 includes a sensor 111 and a user interface 112. The mobile device 110 also includes a computer-readable medium 113 and computer processors 117. The computer-readable medium includes computer-executable instructions 114. The computer-executable instructions 114 include an operating system 115 and an augmented reality (AR) application 116. The medical device 120 includes a plurality of components 121, a plurality of human-readable instructions 122, and a controller circuit 123.

The medical device 120 is configured to perform medical functions. As used herein, medical functions refer to one or more of: (1) the diagnosis, prevention, monitoring, treatment, and/or alleviation of disease; (2) the diagnosis, monitoring, treatment, alleviation, or compensation for an injury or handicap; or (3) the investigation, replacement, and/or modification of the anatomy and/or a physiological process. For illustrative purposes, the medical device 120 in the shown embodiment is a dialysis machine configured to provide dialysis treatment, such as hemodialysis or peritoneal dialysis, and/or other renal replacement therapy, such as hemofiltration or hemodiafiltration. The medical device 120 includes a plurality of components 121 that work together to allow the medical device 120 to perform medical functions. For example, in the shown embodiment, the components 121 of the medical device 120 include several dialysis machine components. The dialysis machine components can include, for example, dialyzers, blood pumps, deaeration tanks, blood pressure cuffs, monitors, brakes, shunt interlocks, pressure gauges, flowmeters, dialysate pumps, clamps, etc.

Each of the plurality of human-readable instructions 122 is associated with at least one component of the plurality of components 121. Hereinafter, the term human-readable refers to representations of data and/or information that can be naturally interpreted by humans, such as visualizations (e.g., graphs, maps, imagery, etc.), numbers/symbols from a language that humans use (e.g., English, French, Japanese, Arabic, etc.), and/or data that is summarized/abstracted to an appropriate level for human comprehension (e.g., visual alerts, audible alerts, etc.), and implies information that has meaning to humans. The plurality of human-readable instructions 122 include text, images, and/or holographic designs. The plurality of human-readable instructions 122 include partial or full instructions on how to use, set up, and/or troubleshoot the components 121 with which the human-readable instructions 122 are associated. For example, in an embodiment, the plurality of components 121 include a dialyzer and the plurality of human-readable instructions 122 include text and/or images partially describing how to configure the dialyzer and set the dialyzer in a holding chamber of the medical device 120. In an embodiment, the plurality of components 120 include medical lines and the plurality of human-readable instructions 122 include text and/or images partially describing how to install the medical lines. In an embodiment, each of the plurality of human-readable instructions 122 include one or more visual tags. In an embodiment, the one or more visual tags are recognizable by CMOS and/or CCD cameras. Although the plurality of human-readable instructions 122 are described as human-readable, the visual tags can be human-readable, machine-readable, or both. For example, the visual tags can include alphanumeric text, barcodes, radio-frequency (RF) tags, resonant tags, and/or infrared tags (e.g., infrared beacon). The visual tags can be printed or non-printed. In an embodiment, all visual tags included in the plurality of human-readable instructions 122 are printable. However, the plurality of human-readable instructions 122 can include only non-printable tags (e.g., RF tags and/or infrared beacons), or the plurality of human-readable instructions 122 can include a combination of printable and non-printable tags.

The mobile device 110 can be one of several types of mobile devices. For example, in the illustrated embodiment, the mobile device 110 is a cellular phone (e.g., smart phone). In an embodiment, the mobile device 110 is a tablet personal computer (PC). The mobile device 110 can also be a wireless wearable interface device, such as a wrist-worn display and/or a head-mounted display. The mobile device 110 is configured to provide various functionalities. For example, in an embodiment, the mobile device 110 is configured to provide voice calls and text messaging. In an embodiment, the mobile device 110 is configured to display photographs and/or videos. In an embodiment, the mobile device 110 is configured to play music and other forms of audio. The mobile device 110 can also be configured to send and receive e-mails, capture and display photographs, capture and display videos, access websites, and display websites.

In an embodiment, the sensor 111 is configured to capture image data. In an embodiment, the sensor 111 is a camera. The camera can capture image data in the form of still images and/or video. The image data can take the form of several image data formats, such as RAW, JPEG, PNG, etc. In an embodiment, the sensor 111 is a digital camera that uses a charged-coupled device (CCD) and/or complementary metal oxide semiconductor (CMOS) to convert photons to electrons for digital processing. In an embodiment, the sensor 111 is a laser scanner. The sensor 111 can also be an LED scanner, an imaging scanner, and/or a radio frequency identification (RFID) scanner. Although the mobile device 110 is shown with only one sensor 111, the mobile device 110 can include several sensors 111 of several types. For example, in an embodiment, the mobile device 110 includes sensors 111 that are a camera and a laser scanner.

In an embodiment, the user interface 112 is a graphical user interface (GUI). The user interface 112 is configured to allow a user of the mobile device 110 to interact with the mobile device 110 through graphical icons and visual indicators. The user interface 112 can use a windows, icons, menus, pointer paradigm (WIMP) to allow a user to interact with the mobile device 110. In an embodiment, the user interface 112 is a touchscreen GUI. The user interface 112 can also use a post-WIMP paradigm typically found in touchscreen-based GUIs. The user interface 112 is configured to display images in the form of still photographs and/or videos.

The computer-readable medium 113 (or computer-readable memory) can include any data storage technology type which is suitable to the local technical environment, including but not limited to semiconductor-based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM), and the like. In an embodiment, the computer-readable medium 113 includes code-segment having executable instructions. In an embodiment, the computer-readable medium 113 stores information corresponding to the components 121 of the medical device 120. The information includes setup, maintenance, and/or troubleshooting instructions (i.e., user-executable instructions) associated with the plurality of components 121 of the medical device 120. For example, in an embodiment, the plurality of components 121 includes a dialyzer and the information includes user-executable instructions on how to set up the dialyzer within a holding chamber of the medical device 120. In an embodiment, the plurality of components 121 includes medical lines and the information includes user-executable instructions on how to perform maintenance on the medical lines. In an embodiment, the plurality of components 121 includes a blood pump and the information includes user-executable instructions on how to troubleshoot the blood pump.

The computer processors 117 are communicatively coupled to the sensor 111. In an embodiment, the computer processors 117 include a general purpose processor. In an embodiment, the computer processors 117 include a central processing unit (CPU). In an embodiment, the computer processors 117 include at least one application specific integrated circuit (ASIC). The computer processors 117 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 117 are configured to execute program code means such as the computer-executable instructions 114. In an embodiment, the computer processors 117 include neural network processors. The neural network processors can perform a variety of machine learning algorithms, such as deep learning techniques (e.g., convolutional, radial basis function, recurrent, and/or modular neural network processing techniques) and/or Bayesian learning techniques.

In an embodiment, the remotely located database 130 is communicatively coupled to the mobile device 110 (e.g., via the computer processors 117) and the medical device 120. The remotely located database 130 is remotely located from the mobile device 110 and/or the medical device 120. Remotely located refers to the situation that the remotely located database is not integrated within the mobile device 110 and/or the medical device 120. For example, the remotely located database can be in the same room as the medical device 120, but not integrated with the medical device 120. In some instances, the remotely located database 130 may not be located proximate to the medical device 120. For example, the remotely located database can be in a different building, a different city, or even a different country than the medical device 120. In an embodiment, the remotely located database 130 is embedded in a cloud computing environment. The medical device 120 is capable of transmitting information about the medical device to the remotely located database 130. In an embodiment, the medical device 120 transmits information regarding historical operational data associated with the one or more of the components 121 (e.g., component failure data, component lifecycle data, component maintenance status data, etc.) For example, if one of the components 121 has experienced a failure in the past, the medical device 120 can transmit data related to the failure to the remotely located database 130. As another example, if one of the components 121 has been used a certain number of times (e.g., has been utilized in 30 or more treatments), the medical device 120 can transmit that information to the remotely located database 130. The medical device 120 can also transmit information associated with the performance of maintenance on one of the components 121 to the remotely located database 130 (e.g., when maintenance occurred, the nature of the maintenance, the extent of the maintenance, the severity of the maintenance, whether the maintenance was fully or partially completed, etc.).

The remotely located database 130 can also receive and store historical information related to the medical device 120 from other sources. In an embodiment, the remotely located database 130 receives and stores maintenance information from other medical devices remote from the medical device 120, information from call centers (e.g., customer service centers) regarding the operation and maintenance of medical devices substantially similar to the medical device 120, and so forth. For example, if a call center receives several calls about the failure (or mistake in set-up) of a particular component 121, the remotely located database 130 can receive data associated with these calls. Thus, the remotely located database 130 can store historical information related to medical devices that are substantially similar to the medical device 120 from sources such as call centers, the information being indicative of common problems with the set-up and maintenance of one or more of the components 121. In an embodiment, the remotely located database 130 can transmit some or all of the information stored with the remotely located database 130 to the computer processors 117.

In an embodiment, the operating system 115 is configured to execute the AR application 116. The operating system 115 may be configured to execute the AR application 116 upon the occurrence of a user-initiated command. A user can, for example, command the operating system 115 to begin executing the AR application 116 by clicking and/or touching an icon representing the AR application 116 on the user interface 112. The operating system 115 can execute the AR application 116 in a foreground state and/or a background state. The AR application 116 can include one or more modes of operation. For example, in an embodiment, the AR application 116 includes a novice mode. In an embodiment, the AR application 116 includes an expert mode.

When the operating system 115 is executing the AR application 116, the computer processors 117 carry out one or more operations. In an embodiment, when the operating system 115 is executing the AR application 116, the computer processors 117 carry out operations to cause the sensor 111 to begin capturing image data associated with the human-readable instructions 122. To facilitate the capturing of image data associated with the human-readable instructions 122, the computer processors 117 can carry out operations to cause the user interface 112 to display a message to a user prompting the user to point the sensor 111 towards the human-readable instructions 122.

In an embodiment, during execution of the AR application 116, the computer processors 117 carry out operations to determine if the captured image data includes at least one of the visual tags included in the human-readable instructions 122. If the captured image data includes one or more tags, the computer processors 117 carry out operations to identify which particular components of the plurality of components 121 of the medical device 120 are associated with the one or more tags included in the captured image data. In an embodiment, if the captured image data includes one or more tags associated with more than one component of the plurality of components 121, the user is prompted to choose a specific component of the plurality of components 121 associated with the captured one or more tags in which the user is interested. As indicated earlier, the visual tags can include, for example, alphanumeric text, barcodes, radio-frequency (RF) tags, resonant tags, and infrared tags (e.g., infrared beacon). In an embodiment, the visual tag is a barcode associated with a specific component 121 of the medical device 120 (e.g., a dialyzer of a dialysis machine). Upon detecting the barcode, the computer processors 117 determine which specific component of the plurality of components 121 is associated with the barcode. In an embodiment, the visual tag is a specific sequence of alphanumeric text associated with a specific component of the plurality of components 121 (e.g., the blood pump of a dialysis machine). In an embodiment, the computer processors 117 detect the specific sequence of alphanumeric text using, for example, optical character recognition (OCR), and determine which specific component of the plurality of components 121 is associated with that specific sequence of alphanumeric text.

In an embodiment, during execution of the AR application 116, the computer processors 117 carry out operations to retrieve, from the computer-readable medium 113, the information associated with the determined components of the plurality of components 121 that correspond with the detected one or more tags. As indicated previously, the information includes user-executable instructions on how to set up, perform maintenance on, and/or troubleshoot the determined components of the plurality of components 121. In an embodiment, the type of information retrieved (i.e., setup instructions, maintenance instructions, and troubleshooting instructions) is based on a user selected mode. For example, in an embodiment, the user is prompted to select one of a setup mode, a maintenance mode, and/or a troubleshooting mode. In an embodiment, if the user selects the setup mode, the computer processors 117 will retrieve information having user-executable instructions corresponding to the setup of the identified component of the plurality of components 121. In an embodiment, if the user selects the troubleshooting mode, the computer processors 117 retrieve information having user-executable instructions corresponding to the troubleshooting of the identified component 122. In an embodiment, if the user selects the maintenance mode, the computer processors 117 retrieve information having user-executable instructions corresponding to performing maintenance on the determined components of the plurality of components 121.

In an embodiment, the computer processors 117 retrieves information based on information received from the remotely located database 130. For example, if information received from the remotely located database 130 is call center information (or information transmitted from remote medical devices) indicative of common mistakes associated with the setup of a particular component of the components 121, the computer processors 117 can retrieve information that includes enhanced setup instructions associated with the particular component. In an embodiment, if the call center information (or remote device information) indicates that an air-line is commonly plugged into a wrong port, the retrieved instructions can include instructions on how to ensure that the air-line is not plugged into the wrong port.

In an embodiment, during execution of the AR application 116, the computer processors 117 carry out operations to cause the user interface 112 to display the information associated with the determined components of the plurality of components 121. In an embodiment, the computer processors 117 cause the user interface 112 to display the user-executable instructions in the form of a static image. The static image can include pictures, drawings, and/or text. For example, in an embodiment, the determined component of the plurality of components 121 is a blood pump and the computer processors 117 cause the user interface 112 to display a series of pictures showing how to troubleshoot the blood pump. In an embodiment, the series of pictures is accompanied by supporting text to help the user understand how to troubleshoot the determined component of the plurality of components 121 (e.g., blood pump). In an embodiment, the computer processors 117 cause the user interface 112 to display the information in the form of an animated image. The animated image can include animated drawings, pre-recorded video, and/or text. For example, in an embodiment, the determined component of the plurality of components 121 is a dialyzer and the computer processors 117 cause the user interface 112 to display an animated drawing showing the steps of setting-up the dialyzer for medical functions. In an embodiment, the computer processors 117 cause the user interface 112 to display the information (e.g., the user-executable instructions) in the form of both static and animated images.

In an embodiment, during execution of the AR application 116, the computer processors 117 carry out operations to cause the user interface 112 to prompt a user to carry out the user-executable instructions included in the displayed information. In an embodiment, during execution of the AR application 116, the computer processors 117 carry out operations to cause the sensor 111 to capture image data associated with the user performing the user-executable instructions. To facilitate the capturing of image data associated with the user performing the user-executable instructions, the computer processors 117 can cause the user interface 112 to prompt the user to focus the sensor 111 on the component of the plurality of components 121 associated with the displayed user-executable instructions.

In an embodiment, during execution of the AR application 116, the computer processors 117 carry out operations to generate feedback based on the data associated with the user performing the user-executable instructions and then cause the user interface 112 to display the feedback to the user. For example, in an embodiment the user is prompted to focus the sensor 111 on the component of the plurality of components 121 associated with the displayed user-executable instructions (the "associated component") after the user believes they have completed the user-executable instructions. In an embodiment, the computer processors 117 then determine if the associated component of the plurality of components 121 has been set up correctly based on the image data captured by the sensor 111.

If the computer processors 117 determine that the associated component of the plurality of components 121 has been set up correctly, the computer processors 117 can cause the user interface 112 to inform the user that the associated component of the plurality of components 121 is set up correctly. If the computer processors 117 determine that the associated component of the plurality of components 121 has not been set up correctly, the computer processors 117 can cause the user interface 112 to inform the user that the associated component of the plurality of components 121 has not been set up correctly. The computer processors 117 can also cause the user interface 112 to redisplay the user-executable instructions or display. In an embodiment, the computer processors 117 determine the specific problems with the incorrect setup of the associated component of the plurality of components 121, and then generate targeted feedback based on the identified specific problem. For example, the computer processors 117 can determine that the venous line of a dialysis machine is connected to the wrong port of the machine's dialyzer, in which case the computer processors 117 can generate feedback that informs the user that the venous line is connected to the wrong port. The feedback can include text and/or images.

In an embodiment, the computer processors 117 are communicatively coupled with the controller circuit 123. As previously indicated, the AR application 116 can be executed in a novice mode. In an embodiment, the AR application 116 is executed in a novice mode based on the selection of a user of the medical device 120. In an embodiment, the AR applications 116 is executed in a novice mode based on historical setup information associated with the user of the medical device 120. For example, the computer processors 117 can receive, from the remotely located database 130, information regarding the users experience level based on the user's previous attempts to setup the medical device 120.

In an embodiment, when AR application 116 is being executed in the novice mode, the computer processors 117 carry out operations to send an idle control signal to the controller circuit 123. In response to receiving the idle control signal, the controller circuit 123 causes the medical device 120 to operate in an idle mode. While operating in idle mode, the controller circuit 123 disables the medical device's 120 ability to perform medical functions. For example, the controller circuit 123 can power-down the medical device 120 upon receiving the idle control signal, or disable one or more components of the plurality of components 121 of the medical device 120.

In an embodiment, when AR application 116 is being executed in the novice mode, the computer processors 117 carry out operations to analyze the image data associated with the user performing the user-executable instructions and determine whether or not the medical device 120 has been properly configured to perform medical functions. To facilitate this, the computer processors 117 can cause the user interface 112 to prompt the user to focus the sensor 111 on one or more components of the plurality of components 121. The computer processors 117 can then determine if each of the one or more components of the plurality of components 121 are set up correctly. In an embodiment, when AR application 116 is being executed in the novice mode, the computer processors 117 carry out operations to send an operate control signal to the controller circuit 123 when the computer processors 117 determine that the medical device 120 is properly configured to perform medical functions. In response to receiving the operate control signal, the controller circuit 123 causes the medical device 120 to operate in a functional mode. While operating in functional mode, the controller circuit 123 enables the medical device's 120 ability to perform medical functions. For example, the controller circuit 123 can power-on the medical device 120 upon receiving the operate control signal, or enable one or more components of the plurality of components 121 of the medical device 120. Consequently, when operating in novice mode, the AR application 116 can ensure that the user does not operate the medical device 120 unless the medical device 120 is properly configured to perform its associated medical functions in a safe manner.

Figure 2A:
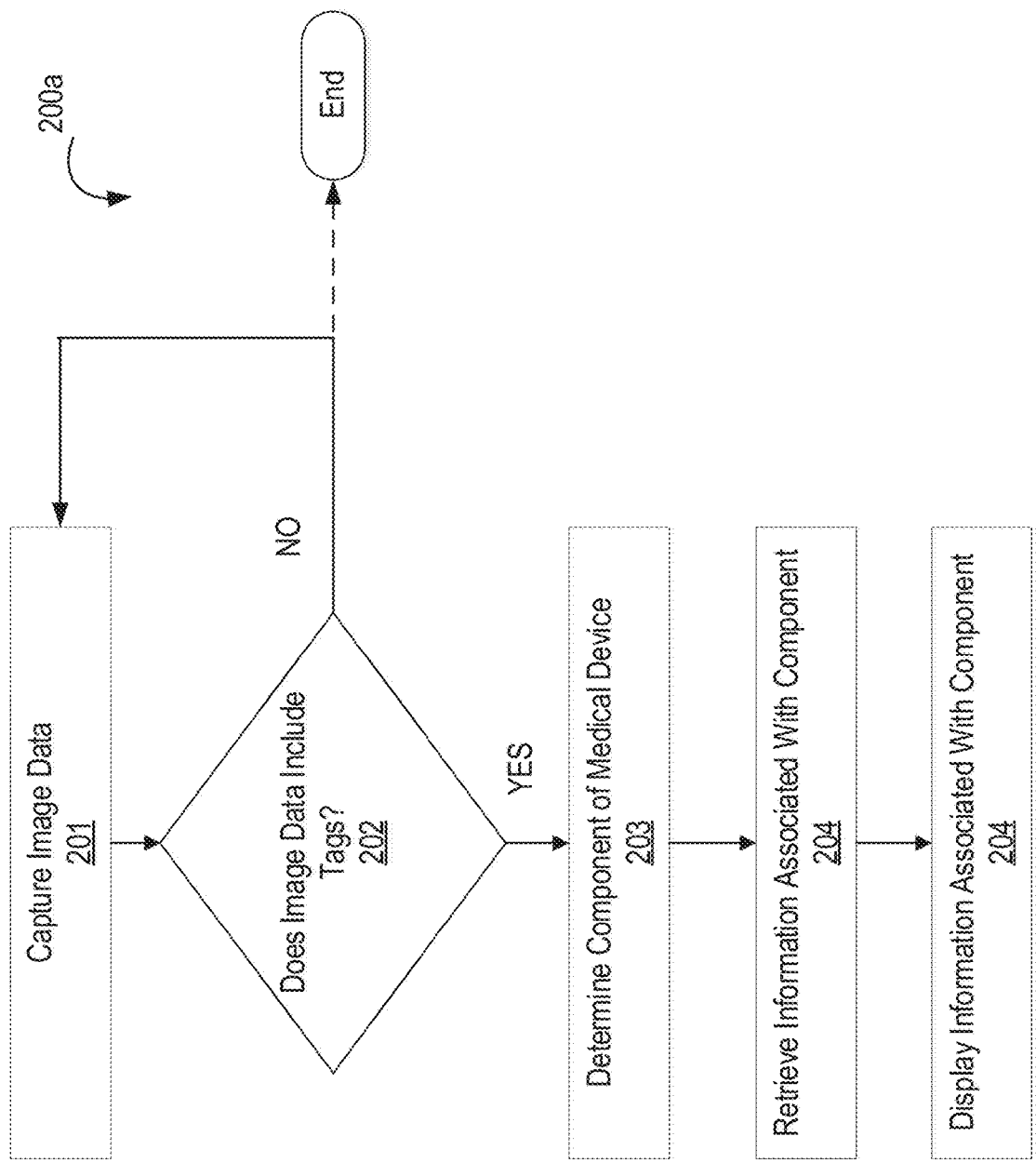
FIG. 2A shows a flowchart depicting an example of a method for providing augmented reality-based training for medical devices, in accordance with one or more embodiments of the present disclosure.

FIG. 2A shows a flowchart depicting an example of a method 200a for providing augmented reality-based training for medical devices, in accordance with one or more embodiments of the present disclosure. For illustrative purposes, the system 100 for providing augmented reality-based training for medical devices performs the method 200a. However, the method 200a may be performed by other systems that allow for augmented reality based training and troubleshooting on medical devices. The method 200a includes capturing image data (block 201) and determining whether the image data includes tags (block 202). If the image data does not include tags, the method 200a includes either ending the method or continuing the capture of image data (block 201). If the image data does include tags, the method 200a includes determining a component of the medical device (block 203), retrieving information associated with the component (block 204), and displaying information associated with the component (block 205).

The method 200a includes capturing image data (block 201). The computer processors 117 carry out operations to cause the sensor 111 to begin capturing image data associated with the human-readable instructions 122. To facilitate the capturing of this image data, the computer processors 117 can carry out operations to cause the user interface 112 to prompt the user (e.g., in the form of a text-based message or graphical icon) to focus the sensor 111 towards the human-readable instructions 122 on the medical device 120.

The method 200a includes determining whether the image data includes tags (block 202). As indicated earlier, the human-readable instructions 122 can include one or more visual tags, each being associated with a specific component of the plurality of components 121 of the medical device 120. The computer processors 117 carry out operations to determine if the captured image data (from block 201) includes at least one of the visual tags included within the human-readable instructions 122.

If the image data does not include tags, the method 200a includes either ending the method or continuing the capture of image data (block 201). In an embodiment, if the image data does not include at least one visual tag, the computer processors 117 will cause the sensor 111 to continue the capture of image data (block 201) for a predetermined amount of time (e.g., 10 seconds, 20 seconds, 30 seconds, etc.), and if the captured image data does not include at least one visual tag in the predetermined amount of time, the operating system 115 will discontinue executing the AR application 116. The predetermined amount of time can be user selected and/or a manufactured design choice based on, for example, power saving considerations.

If the image data does include tags, the method 200a includes determining a component of the medical device (block 203). The computer processors 117 carry out operations to identify which components of the plurality of components 121 of the medical device 120 is associated with the one or more visual tags included in the captured image data. As indicated earlier with reference to FIG. 1, the visual tags can include, for example, alphanumeric text, barcodes, radio-frequency (RF) tags, resonant tags, and infrared tags (e.g., infrared beacon). The visual tag can be a barcode associated with a specific component of the plurality of components 121 (e.g., a dialyzer of a dialysis machine). In this instance, upon detecting the barcode, the computer processors 117 determine which specific component of the plurality of components 121 of the medical device 120 is associated with the barcode (the "associated component"). As another example, the tag can be a specific sequence of alphanumeric text associated with a specific component of the plurality of components 121 (e.g., the blood pump of a dialysis machine). In this instance, the computer processors 117 detect the specific sequence of alphanumeric text using, for example, optical character recognition (OCR) and determine which specific component of the plurality of components 121 is associated with that specific sequence of alphanumeric text. If there are two or more components of the plurality of components 121 associated with the detected one or more visual tags, the user can be prompted to select a specific component of the plurality of components 121 in which the user is interested. For example, assume that the captured image data includes a visual tag associated with a blood pump and a visual tag associated with a dialyzer. The user can be prompted to choose either the blood pump or the dialyzer based on the particular component in which the user is interested (e.g., for performing set up, maintenance, and/or troubleshooting).

If the image data does include tags, the method 200a includes retrieving information associated with the component (block 204). As indicated earlier, the computer-readable medium 113 stores information associated with one or more components of the plurality of components 121 of the medical device 120. The information can include user-executable instructions corresponding to the setup, maintenance, and/or troubleshooting for each component of the plurality of components 121 of the medical device 120. The computer processors 117 retrieve the information associated with the component of the plurality of components 121 that was identified in block 203 from the computer-readable medium 113 (the "associated component"). For example, if the associated component of the plurality of components 121 identified in block 203 is a dialyzer, the computer processors 117 can retrieve the information associated with the dialyzer. The type of information retrieved (i.e., setup instructions, maintenance instructions, and troubleshooting instructions) can be based on a user selected mode. For example, the user can select a setup mode, and the computer processors 117 will retrieve information having user-executable instructions corresponding to the setup of the associated component of the plurality of components 121. The user can select a troubleshooting mode, and the computer processors 117 will retrieve information having user-executable instructions corresponding to the troubleshooting of the associated component of the plurality of components 121. The user can select a maintenance mode, and the computer processors 117 will retrieve information having user-executable instructions corresponding to performing maintenance on the associated component of the plurality of components 121.

If the image data does include tags, the method 200a includes displaying information associated with the component (block 205). The computer processors 117 carry out operations to cause the user interface 112 to display the information corresponding to the associated component of the plurality of components 121. In an embodiment, the computer processors 117 cause the user interface 112 to display the user-executable instructions in the form of a static image. The static image can include pictures, drawings, and/or text. For example, in an embodiment, the computer processors 117 cause the user interface 112 to display a series of pictures showing how to troubleshoot a blood pump of a dialysis machine. The series of pictures can be accompanied by supporting text to help the user understand how to troubleshoot the blood pump. In an embodiment, the computer processors 117 cause the user interface 112 to display the information in the form of an animated image. The animated image can include animated drawings, pre-recorded video, and/or text. For example, in an embodiment, the associated component of the plurality of components is a dialyzer and the computer processors 117 cause the user interface 112 to display an animated drawing showing the steps of setting-up the dialyzer. In an embodiment, the associated component of the plurality of components 121 is a medical line and the computer processors 117 cause the user interface 112 to display a pre-recorded video showing the steps of connecting medical lines to a dialyzer. The computer processors 117 can also cause the user interface 112 to display the information in the form of both static and animated images.

Figure 2B:
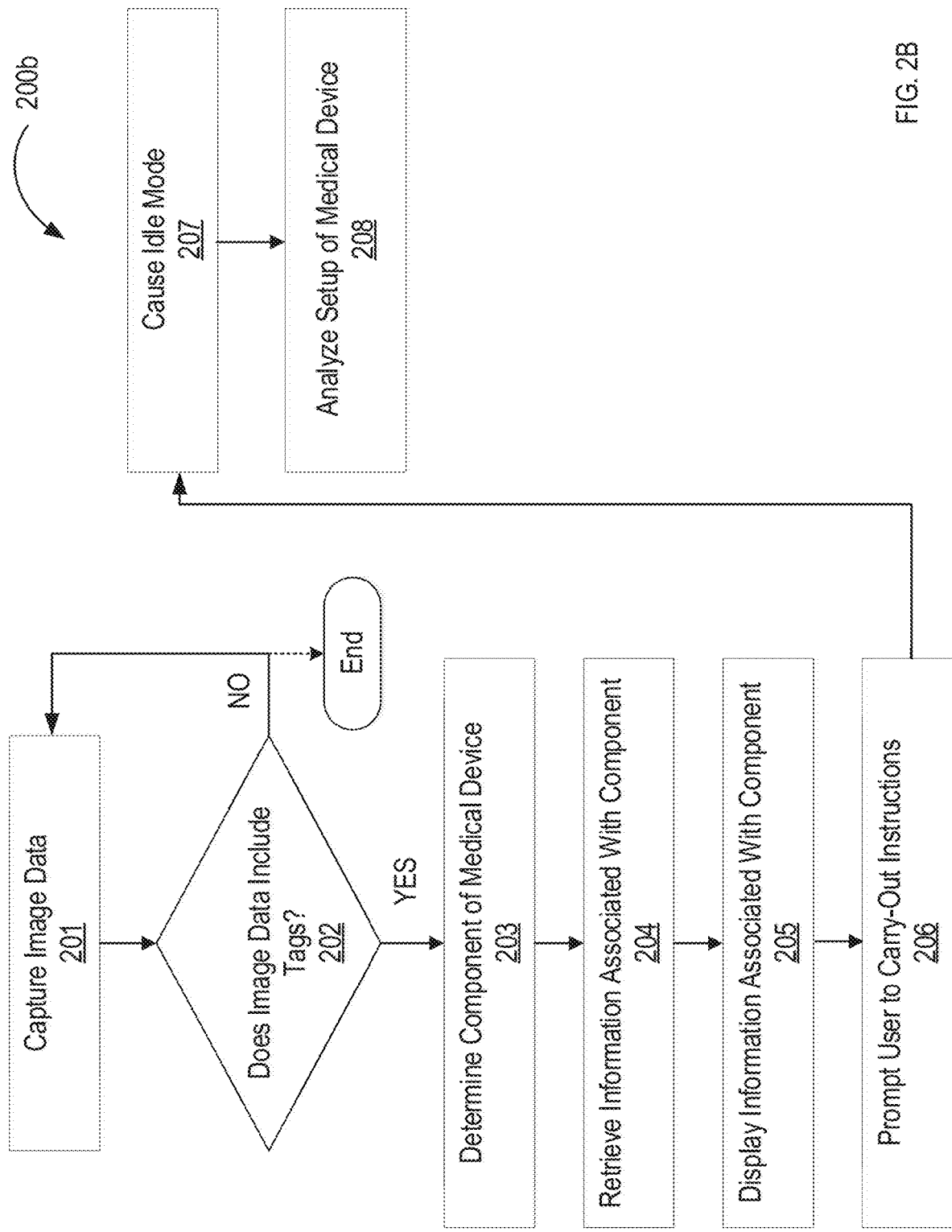
FIG. 2B shows a flowchart depicting an example of a method for providing augmented reality-based training and analysis for medical devices, in accordance with one or more embodiments of the present disclosure.

FIG. 2B shows a flowchart depicting an example of a method 200b for providing augmented reality-based training and analysis for medical devices, in accordance with one or more embodiments of the present disclosure. For illustrative purposes, the system 100 for providing augmented reality-based training for medical devices performs the method 200b. However, the method 200b may be performed by other systems that allow for augmented reality-based training and troubleshooting on medical devices. The method 200b includes capturing image data (block 201), determining whether the image data includes tags (block 202), determining a component of the medical device (block 203), retrieving information associated with the component (block 204), and displaying information associated with the component (block 205). Blocks 201-205 were previously described in the method 200a for providing augmented reality-based training for medical devices with reference to FIG. 2A. The method 200b further includes prompting the patient to carry-out instructions (block 206), causing idle mode (block 207), and analyzing device setup (block 208).

The method 200b includes prompting the user to carry-out instructions (block 206). The computer processors 117 cause the user interface 112 to prompt the user to carry-out the user-executable instructions that were retrieved and displayed in blocks 204-205. In an embodiment, the prompt includes text-based messages, graphical icons, vibrations and/or alert sounds.

The method 200b includes causing idle mode (block 207). As indicated earlier with reference to FIG. 1, the computer processors 117 can be communicatively coupled to the controller circuit 123 of the medical device 120. In an embodiment, the computer processors 117 send an idle control signal to the controller circuit 123. In an embodiment, once the idle control signal is received by the controller circuit 123, the controller circuit 123 causes the medical device 120 to operate in an idle mode. Causing the medical device 120 to operate in idle mode can include powering-down the medical device 120 and/or disabling one or more components of the plurality of components 121 of the medical device 120. For example, in an embodiment, the controller circuit 123 powers-down the entire medical device 120 upon receiving the idle control signal. In an embodiment, the controller circuit 123 disables one or more components of the plurality of components 121 (e.g., disabling the blood pump of a dialysis machine).

Figure 2C:
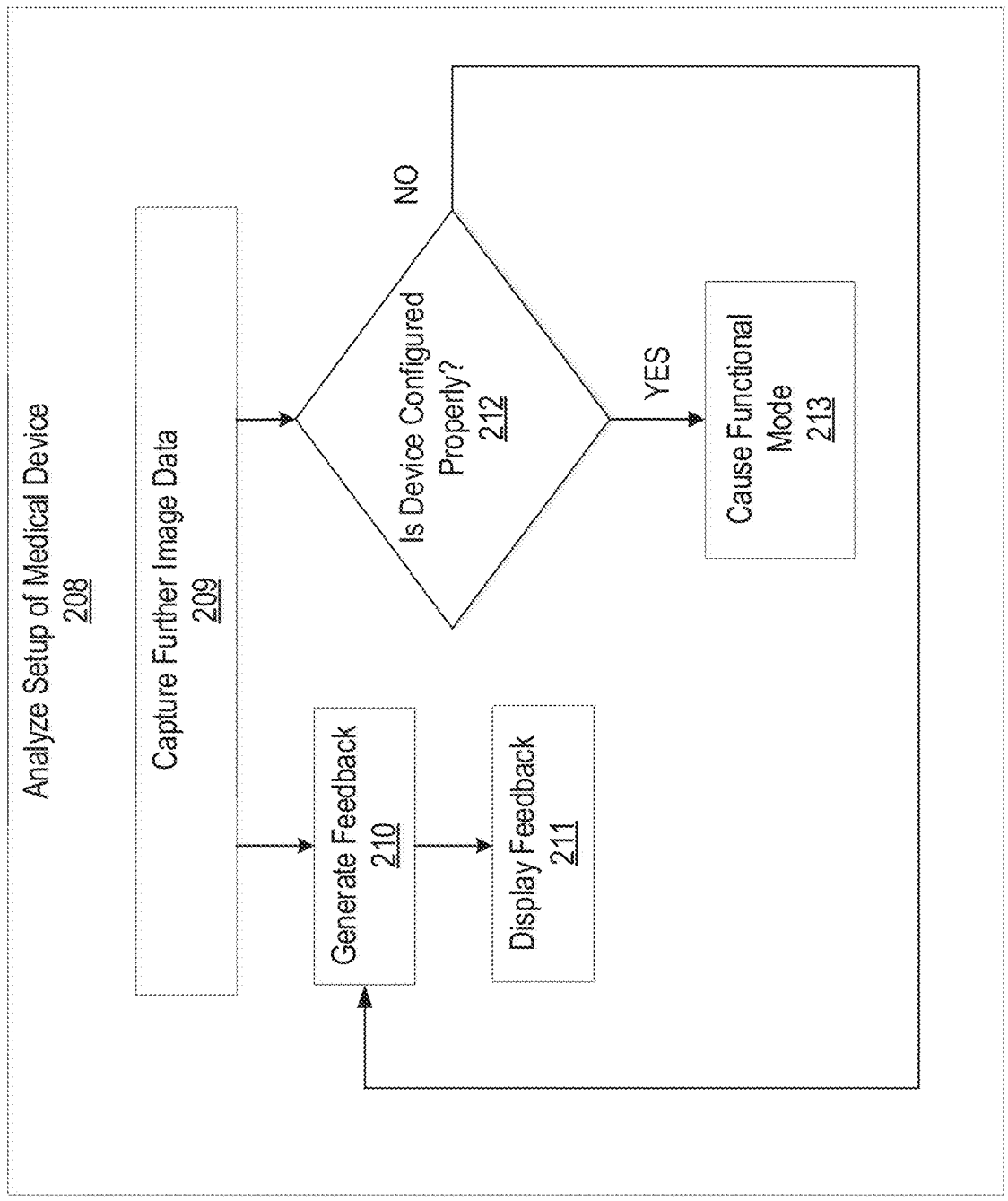
FIG. 2C shows flowchart depicting an example of analyzing the setup of a medical device used in a method for providing augmented reality-based training and analysis for medical devices, in accordance with one or more embodiments of the present disclosure.

The method 200b includes analyzing the setup of the device (block 208). FIG. 2C shows flowchart depicting an example of analyzing the setup of a medical device (block 208) used in the method 200b for providing augmented reality-based training and analysis for medical devices, in accordance with one or more embodiments of the present disclosure. Analyzing the setup of the device (block 208) includes capturing further image data (block 209). In an embodiment, analyzing the setup of the device (block 208) includes generating feedback (block 210) and displaying the feedback (block 211). In an embodiment, analyzing the setup of the device (block 208) includes determining if the medical device is properly configured (block 212). If it is determined that the medical device is properly configured, analyzing the setup of a medical device (block 208) includes causing functional mode (block 213). In an embodiment, if it is determined that the medical device is not properly configured, analyzing the setup of the medical device (block 208) includes generating feedback (block 210) and displaying the feedback (block 211).

Analyzing the setup of the device (block 208) includes capturing further image data (block 209). The computer processors 117 carry out operations to capture image data associated with the user performing the user-executable instructions. To facilitate this, the computer processors 117 can cause the user interface 112 to prompt the user to focus the sensor 111 on one or more components of the plurality of components 121 of the medical device 120. For example, in an embodiment, the user interface 112 prompts the user to focus on one or more components of the plurality of components 121 after the user confirms completion of the displayed user-executable instructions associated with the one or more components (the "associated components") of the plurality of components 121. In an embodiment, the user is prompted to focus the sensor 111 on all of the components of the plurality of components 121 of the medical device 120. In an embodiment, the user is prompted to focus the sensor 111 on a select number of components of the plurality of components 121 of the medical device 120. The select number of components can be selected based on user preference or design choices based on, for example, safety considerations (e.g., the importance of the components with regard to the safe performance of medical functions).

In an embodiment, analyzing the setup of the device (block 208) includes generating feedback (block 210). The computer processors 117 can analyze the captured image data associated with the user performing the user-executable instructions, and based on this analysis, generate feedback for the user. For example, based on the captured image data of the associated one or more components of the plurality of components 121, the computer processors 117 can analyze the captured image data to determine if the user-executable instructions were executed correctly. If the user executed the user-executable instructions correctly, the computer processors 117 can generate feedback confirming that the user-executable instructions were correctly followed. If the computer processors 117 determine that the user-executable instructions were not followed correctly, the computer processors 117 can generate feedback confirming that the user-executable instructions were not correctly followed. In an embodiment, the computer processors 117 generate targeted feedback based on analysis of the image data. For instance, in an embodiment, the computer processors 117 can determine what specifically the user did wrong when executing the user-executable instructions, and generate feedback based on the specific wrongdoing.

Figure 7B:
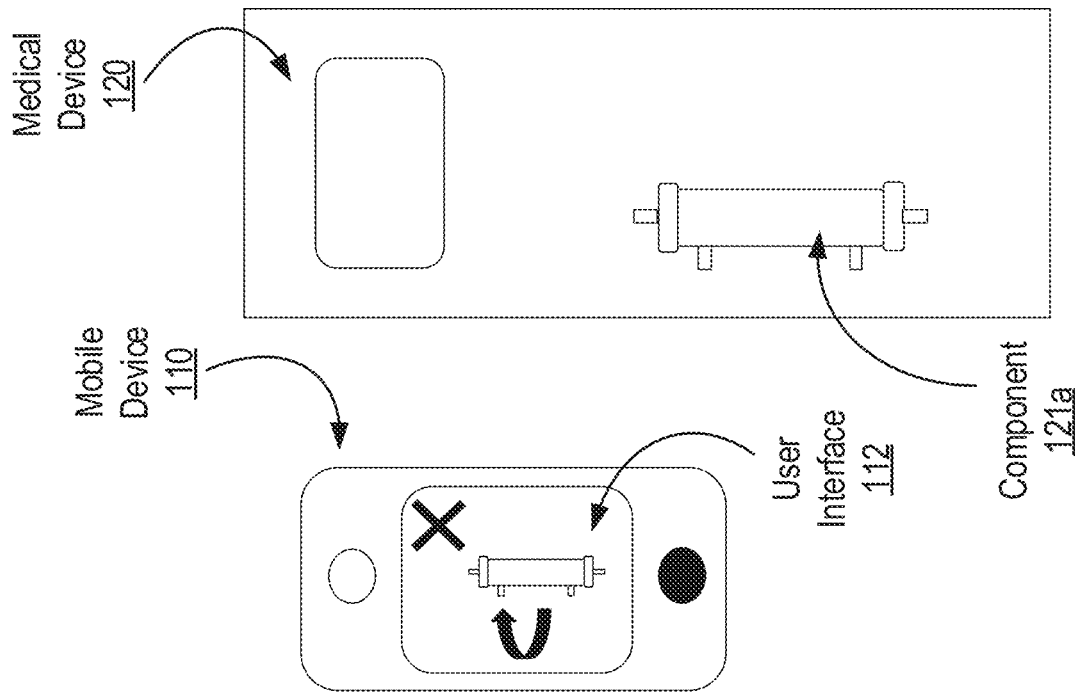
FIGS. 7A-7B are illustrations showing a mobile device providing a user with visual feedback based on analyzing the setup of a medical device, according to one or more embodiments of the present disclosure.
Figure 7A:
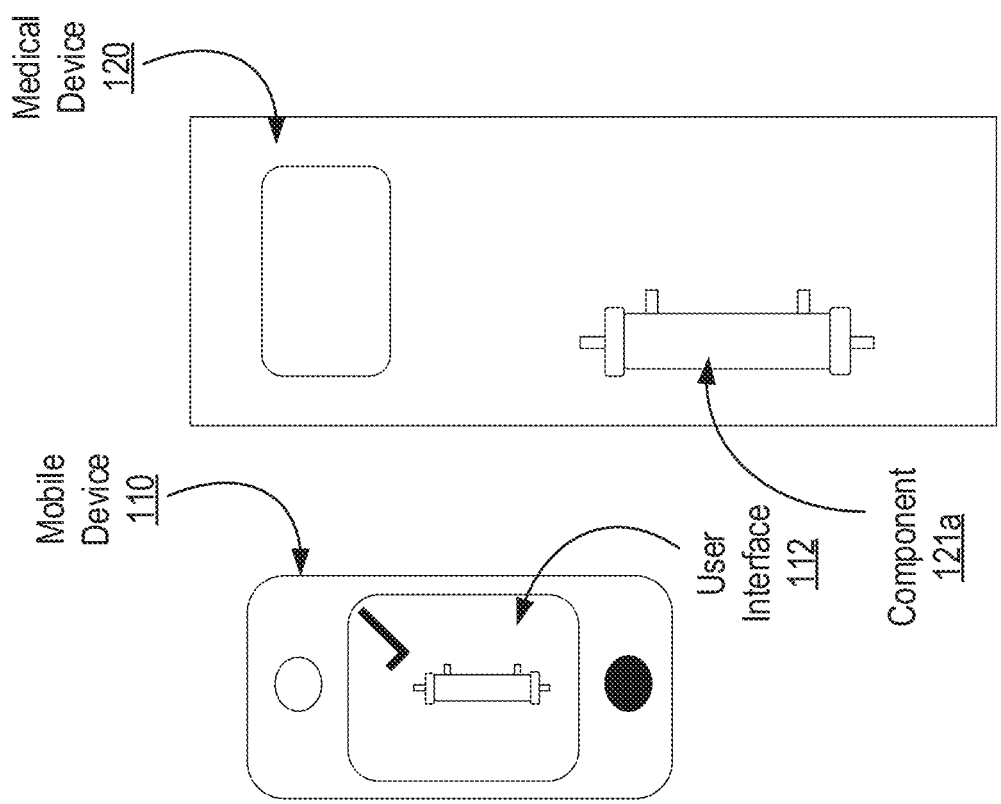

As an example, FIGS. 7A-7B are illustrations showing the mobile device 110 providing a user with visual feedback based on analyzing the setup of the device, according to one or more embodiments of the present disclosure. Referring to FIG. 7A, when the computer processors 117 determine that a component 121a is set up correctly, the mobile device 110 provides illustrative feedback to a user via the user interface 112 confirming that the component 121a of the medical device 120 is correctly set up. Referring to FIG. 7B, when the computer processors 117 determine that the component 121a is set up incorrectly, the mobile device 110 provides illustrative feedback to a user via the user interface 112 notifying the user that the component 121a of the medical device 120 is set up incorrectly. In the case of an incorrect set up, the user is instructed through illustrative feedback via the user interface 112 how to fix the incorrectly set up component 121a based on an identified specific wrongdoing (e.g., the component 121a is set up backwards). As another example, assume that while setting up the dialyzer of a dialysis machine, the user connects the venous line into the wrong side of the dialyzer. Based on the received image data, the computer processors 117 can determine that the venous line has been attached to the wrong end of the dialyzer and generate feedback detailing how to connect the venous line to the appropriate end of the dialyzer.

In an embodiment, analyzing the setup of the device (block 208) includes displaying feedback (block 211). The computer processors 117 cause the user interface 112 to display the feedback generated in block 210. In an embodiment, displaying the feedback includes displaying one or more still images. In an embodiment, if the generated feedback is confirming the correct setup of one or more components of the plurality of components 121 of the medical device 120, the displayed feedback includes textual messages, graphical icons, and/or sound alerts representing confirmation of a correct setup. In an embodiment, if the generated feedback is confirming an incorrect setup of the one or more components 121 of the medical device 120, the displayed feedback includes textual messages, graphical icons, or sound alerts representing confirmation of an incorrect setup. In an embodiment, if the generated feedback is confirming an incorrect setup of one or more components of the plurality of components 121 of the medical device 120, the displayed feedback can include an overlay on the captured images of the one or more components of the plurality of components 121 that direct the user as to what specifically is wrong with the setup of a particular component. For example, assume that the user connected a medical line, such as an arterial line, to the wrong port on the dialyzer of a dialysis machine. The displayed feedback can include the captured image of the dialyzer with the arterial line connected to the wrong port, with a graphical rectangle outlining the arterial line connected to the wrong port, along with other graphical features (e.g., arrows, lines, etc.) directing the user to the correct port for the arterial line connection. In an embodiment, if the generated feedback is confirming an incorrect setup of one or more components of the plurality of components 121 of the medical device 120, the displayed feedback can include pre-recorded videos and/or pre-captured images showing the correct setup of the one or more components of the plurality of components 121 of the medical device 120.

In an embodiment, analyzing the setup of the medical device (block 208) includes determining if the device is configured properly (block 212). Once the computer processors 117 determine that each component of the plurality of components 121 of the medical device 120 (or alternatively, a predefined number and/or type of components of the plurality of components 121 of the medical device 120) are set up correctly, the computer processors 117 determine that the medical device 120 is properly configured to perform medical functions. In an embodiment, if the computer processors 117 determine that one or more components of the plurality of components 121 are not set up correctly, the computer processors 117 generate and display feedback (blocks 210 and 211) instructing the user how to correctly set up the incorrectly configured components 121. In an embodiment, the computer processors 117 will continue to perform blocks 209, 210, and 211 until the computer processors determine that the medical device 120 is properly configured for performing medical functions.

In an embodiment, analyzing the setup of the medical device (block 208) includes causing functional mode (block 213). In an embodiment, the computer processors 117 carry out operations to send an operate control signal to the controller circuit 123 when the computer processors 117 determine that the medical device 120 is properly configured to perform medical functions. In an embodiment, in response to receiving the operate control signal, the controller circuit 123 causes the medical device 120 to operate in a functional mode. In an embodiment, while operating in functional mode, the controller circuit 123 enables the medical device's 120 ability to perform medical functions. For example, the controller circuit 123 can power-on the medical device 120 upon receiving the operate control signal, and/or enable (e.g., power-on) one or more components of the plurality of components 121 of the medical device 120.

Figure 3:
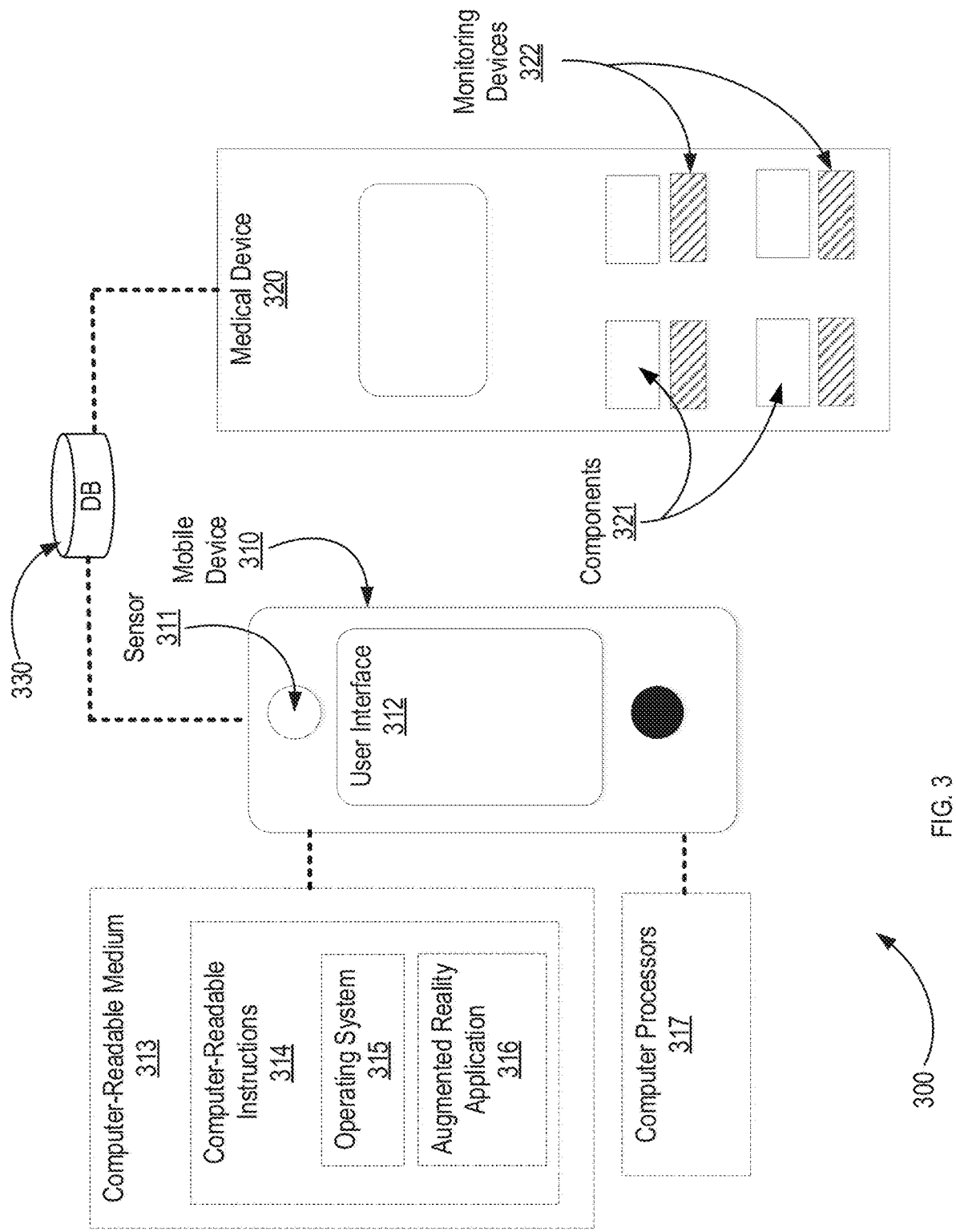
FIG. 3 shows an example of a system for providing augmented reality-based troubleshooting for medical devices, in accordance with one or more embodiments of the present disclosure.

FIG. 3 shows an example of a system 300 for providing augmented reality-based troubleshooting for medical devices, in accordance with one or more embodiments of the present disclosure. The system 300 includes a mobile device 310, a medical device 320, and a remotely located database 330. The mobile device 310 includes a sensor 311 and a user interface 312. The mobile device 310 also includes a computer-readable medium 313 and computer processors 317. The computer-readable medium includes computer-executable instructions 314. The computer-executable instructions 314 include an operating system 315 and an augmented reality (AR) application 316. The medical device 320 includes a plurality of components 321 and a plurality of monitoring devices 322. In an embodiment, the remotely located database 330 is substantially similar to the remotely located database 130 discussed previously with reference to FIG. 1.

The medical device 320 is configured to perform medical functions. For illustrative purposes, the shown medical device 320 is a dialysis machine configured to provide dialysis treatment, such as hemodialysis or peritoneal dialysis, and/or other renal replacement therapy, such as hemofiltration or hemodiafiltration. The medical device 320 includes a plurality of components 321 that work together to allow the medical device 320 to perform medical functions. For example, in the shown embodiment, the components 321 of the medical device include several dialysis machine components. The dialysis machine components can include, for example, dialyzers, blood pumps, deaeration tanks, blood pressure cuffs, monitors, brakes, shunt interlocks, pressure gauges, flowmeters, dialysate pumps, clamps, etc.

Each monitoring device of the plurality of monitoring devices 322 are associated with one or more components of the plurality of components 321. Each of the monitoring devices of the plurality of monitoring devices 322 is configured to measure, monitor, and/or detect one or more operational parameters of at least one component of the plurality of components 321. Each monitoring device of the plurality of monitoring devices 322 can be one of several types of devices configured to monitor components of a medical device. In an embodiment, the plurality of monitoring devices 322 include thermometers, pressure gauges, motion detectors, chemical detectors, pH readers, conductivity sensors, infrared sensors, and/or light sensors. In an embodiment, for example, the plurality of components 321 includes a dialyzer and the monitoring devices 322 include an infrared sensor located downstream from the dialyzer. The infrared sensor can be configured, for instance, to detect an amount of blood (i.e., operational parameter) that crosses the blood/dialysate membrane of the dialyzer. In an embodiment, the plurality of components 321 include a dialysate compartment and/or a blood compartment and the monitoring devices 322 include pressure sensors configured to measure the pressure (i.e., operational parameter) in the dialysate compartment and/or the blood compartment. In an embodiment, the plurality of components 321 include heating elements and the plurality of monitoring devices 322 include a temperature sensor to measure the operating temperature (i.e., operational parameter) associated with the heating element. In an embodiment, the plurality of components 321 includes a dialyzer, and the plurality of monitoring devices 322 include flow sensors on the inlet and/or outlet side of the dialyzer configured to measure the flow (i.e., operational parameter) of dialysate to and/or from the dialyzer.

In an embodiment, the monitoring device 322 includes display devices. In an embodiment, the display devices present specific images associated with one or more operational parameters of at least one component of the plurality of components 321. For example, the display devices can present images associated the temperature of a heating element, the flow of dialysate from a dialyzer, and so forth. In an embodiment, the monitoring devices 322 include one or more alert modules configured to produce audible and/or visual alerts (e.g., beeping sounds and/or flashing red lights) associated with the one or more operational parameters. For example, if the temperature of a heating element exceeds a threshold temperature value, the alter modules can produce a beeping sound (e.g., using speakers) and/or a flashing red light (e.g., using an LED light beacon). In an embodiment, the audio and/or visual alerts are specific to the operational parameter and/or the magnitude of the operational parameters. For example, the alert module can produce an audio alert having a first pitch when the operational parameters exceeds a first threshold value, and produce an audio alert having a second pitch that is different from the first pitch when the operational parameter exceeds a second threshold value. All of the monitoring devices 322 can use the same alert module or each monitoring device can include their own alert module.

The mobile device 310 can be one of several types of mobile devices. For example, in the illustrated embodiment, the mobile device 310 is a cellular phone (e.g., smart phone). In an embodiment, the mobile device is a tablet personal computer (PC). The mobile device 310 can also be a wireless wearable interface device, such as a head-mounted display. The mobile device 310 is configured to provide various functionalities. In an embodiment, the mobile device 310 is configured to provide voice calls and text messaging. In an embodiment, the mobile device 310 is configured to display photographs and/or videos. In an embodiment, the mobile device 310 is configured to play music and other forms of audio. The mobile device 310 can also be configured to send and receive e-mails, capture and display photographs, capture and display videos, access websites, and display websites.

In an embodiment, the sensor 311 is configured to capture image data. In an embodiment, the sensor 311 is a camera. The camera can capture image data in the form of still images and/or video. The image data can take the form of several image data formats, such as RAW, JPEG, PNG, etc. In an embodiment, the sensor 311 is a digital camera that uses a charged-coupled device (CCD) and/or complementary metal oxide semiconductor (CMOS) to convert photons to electrons for digital processing. In an embodiment, the sensor 311 is a laser scanner. The sensor 311 can also be an LED scanner, an imaging scanner, and/or a radio frequency identification (RFID) scanner. Although the mobile device 310 is shown with only one sensor 311, the mobile device 310 can include more sensors 311 of several types. For example, in an embodiment, the sensors 311 are a camera and a laser scanner. Alternatively, or additionally, the sensor 311 is configured to capture audio data. In an embodiment, the sensor 311 includes a microphone.

In an embodiment, the user interface 312 is a graphical user interface (GUI). The user interface 312 is configured to allow a user of the mobile device 310 to interact with the mobile device 310 through graphical icons and/or visual indicators. The user interface 312 can use a windows, icons, menus, pointer paradigm (WIMP) to allow a user to interact with the mobile device 310. In an embodiment, the user interface 312 is a touchscreen-based GUI. Thus, the user interface 312 can also use a post-WIMP paradigm typically found in touchscreen-based GUIs. The user interface 312 is configured to display images in the form of still photographs and/or videos.

The computer-readable medium 313 (or computer-readable memory) can include any data storage technology type which is suitable to the local technical environment, including but not limited to semiconductor-based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM), and the like. In an embodiment, the computer-readable medium 313 includes code-segment having executable instructions. In an embodiment, the computer-readable medium 313 stores information corresponding to one or more components of the plurality of components 321 of the medical device 320. The information includes setup, maintenance, and/or troubleshooting instructions (i.e., user-executable instructions) associated with the plurality of components 321 of the medical device 320. For example, in an embodiment, the plurality of components includes a dialyzer and the information includes user-executable instructions on how to perform maintenance on the dialyzer when the dialyzer has, for instance, a ruptured membrane. In an embodiment, the plurality of components 321 includes arterial lines, and the information includes user-executable instructions on how to perform maintenance on the arterial lines when the arterial lines are experiencing a decrease in fluid flow. In an embodiment, the plurality of components 321 includes a blood pump, and the information includes user-executable instructions on how to perform maintenance on the blood pump when the blood pump is experiencing low operating pressure.

The computer processors 317 are communicatively coupled to the sensor 311. The computer processors 317 are also communicatively coupled to the medical device 320. In an embodiment, the computer processors 317 include a general purpose processor. In an embodiment, the computer processors 317 include a central processing unit (CPU). In an embodiment, the computer processors 317 include at least one application specific integrated circuit (ASIC). The computer processors 317 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 317 are configured to execute program code means such as the computer-executable instructions 314. In an embodiment, the computer processors 317 include neural network processors. The neural network processors can perform a variety of machine learning algorithms, such as deep learning techniques (e.g., convolutional, radial basis function, recurrent, and/or modular neural network processing techniques) and/or Bayesian learning techniques.

The operating system 315 is configured to execute the AR application 316. In an embodiment, the operating system 315 is configured to execute the AR application 316 upon the occurrence of a user-initiated command. A user can, for example, command the operating system 315 to begin executing the AR application 316 by clicking or touching an icon representing the AR application 316 on the user interface 312. The operating system 315 can execute the AR application 316 in a foreground state and/or a background state. The AR application 316 can include one or more modes of operation. For example, in an embodiment, the AR application 316 includes a novice mode. In an embodiment, the AR application includes an expert mode.

When the operating system 315 is executing the AR application 316, the computer processors 317 carry out one or more operations. In an embodiment, when the operating system 315 is executing the AR application 316, the computer processors 317 carry out operations to receive operational data associated with the one or more operational parameters (e.g., temperature, pressure, amount of fluid, conductance, amount of flow, etc.) of one or more components of the plurality of components 321 from the monitoring devices 322. For example, in an embodiment, the plurality of components 321 include one or more pumps, and the computer processors 317 receive, from the monitoring devices 322, pressure data associated with fluid pressure levels (i.e., operational parameter) of the one or more pumps. In an embodiment, the plurality of components include a dialyzer, and the computer processors 317 receive, from the monitoring device 322, blood detection data associated with an amount of blood (i.e. operational parameter) leaving the dialyzer. In an embodiment, the plurality of components 321 includes one or more heating elements, and the computer processors 317 receive temperature data from the monitoring devices 322 associated with operational temperatures (i.e. operational parameter) of one or more heating elements.

In an embodiment, the operational data is received through direct transmission from the medical device 320. In an embodiment, the operational data is received from the remotely located database 330. In an embodiment, the operational data is received by the sensor 311. For example, as indicated previously, the monitoring devices 322 can produce specific images associated with one or more operational parameters. In some instances, the sensor 311 is capable of capturing the specific images and the computer processors 317 are capable of determining, based on the captured specific images, values associated with the one or more operational parameters. Also, as previously indicated, the monitoring devices can produce audio alerts associated with one or more operational parameters. In some instances, the sensor 311 is capable of capturing the audio alerts and the computer processors 317 are capable of determining, based on the capture audio alert, values associated with the one or more operational parameters. The use of the specific images/audio alerts along with the sensor 311 to capture the one or more parameters can increase the security of the system 300 by making the system 300 less vulnerable to outside threats (e.g., hackers) because the information is not sent through communication portals (e.g., bluetooth and/or WiFi portals) that are susceptible to cyber penetration.

In an embodiment, during the execution of the AR application 316, the computer processors 317 carry out operations to determine if one or more components of the plurality of components 321 are experiencing a failure based on the received operational data. The failure can be full or partial. For example, in an embodiment, the plurality of components includes a dialyzer. If the operational data indicates that blood was detected downstream from the dialyzer, the computer processors 317 determine that the dialyzer is experiencing a failure. In an embodiment, if the blood detection data indicates that more than a threshold amount of blood was detected (e.g., 5 ml, 10 ml, etc.), the computer processors 317 determine that the dialyzer is experiencing a full failure. As another example, in an embodiment, the plurality of components includes one or more heating elements. If the received operational data indicates that fluid flowing through the medical device 320 is below a threshold temperature, the computer processors 317 determine that at least one of the one or more heating elements are experiencing a failure. The computer processors 317 can also analyze the operational data further to determine which specific heating elements of the one or more heating elements are experiencing the failure, or if all of the heating elements are experiencing the failure.

In an embodiment, the computer processors 317 use information received from the remotely located database 130 to determine if a component of the plurality of components 321 is experiencing a failure. For example, the computer processors 317 can receive information from the remotely located database 130 indicative of a particular components lifespan and how many times the particular component has been utilized. The computer processors 317 can also receive information from the remotely located database 330 indicative of common problems related to components of remote medical devices similar to the medical device 320. For example, the information can be transmitted to the remotely located database 330 from call centers or the remote medical devices. The computer processors can then use this historical information to help determine the extent of the component failure. For example, if a call center receives several calls indicating that a particular component is experiencing complete failure after 40 treatment sessions, and a corresponding component of the plurality of components 321 has been used in 40 treatments and is experiencing a failure, the computer processors 317 can determine that the corresponding component is experiencing a full failure.

In an embodiment, during execution of the AR application 316, the computer processors 317 carry out operations to generate a confidence value for each determination that a component of the plurality of components 321 is experiencing a failure. For example, in an embodiment, the plurality of components 321 includes a pump. If the operational data includes data indicating that the pump is experiencing a slight decrease in pressure from a desired pressure value, the computer processors 317 generate a confidence value indicating that the pump is possibly experiencing a failure (e.g., the computer processors 317 are 35% sure that the pump is experiencing a failure.) In an embodiment, if the operational data includes data indicating that the pump is experiencing a large decrease in pressure from an optimal pressure value, the computer processors 317 generate a confidence value indicating that the pump is very likely experiencing a failure (e.g., the computer processors 317 are 85% sure that the pump is experiencing a failure). As indicated previously, the computer processors 317 can utilize machine learning techniques. In an embodiment, the computer processors 317 use machine learning techniques to generate the confidence value based on, for example, historical data and/or shared data (e.g., retrieved from the remotely located database 330). For example, if the operational data includes data indicating that a pump of the medical device 320 is operating at 5% below an optimal pressure value, and historical data and/or shared data (e.g., data received from call centers or data received from other medical devices similar to the medical device 320) indicates that the pump is high likely experiencing a failure when it operates at 5% below an optimal pressure value, the computer processors 317 can generate a confidence value indicating that the pump is highly likely experiencing a failure (e.g., 90%).

In an embodiment, during execution of the AR application 316, the computer processors 317 carry out operations to generate user-executable instructions if the computer processors 317 determine that one or more components of the plurality of components 321 are experiencing a failure (the "failing components). The user-executable instructions correspond to the failing components of the plurality of components 321. In an embodiment, the user-executable instructions include general troubleshooting instructions associated with the failing components of the plurality of components 321. For example, in response to operational data indicating high return pressure of a return pump in a dialysis circuit, the user-executable instructions can include instructions on how to perform general visual checks on each feature of the circuit. In an embodiment, the user-executable instructions includes specific instructions associated with how to fix the failing components of the plurality of components 321, based at least partially on the received operational data. For example, in response to operational data indicating high filter pressure associated with a filter of the medical device 320, the user-executable instructions can include how to ensure the filter line is free from kinks (e.g., bends, curves, knots, etc.), how to ensure that the filter lines do not include clamps, and/or how to ensure that an appropriate fluid flow rate (e.g., appropriate based on safety considerations) has been selected, based on the magnitude of the indicated high filter pressure.

In an embodiment, the computer processors 317 include machine learning processors and/or deep learning neural networks to facilitate the determining if the one or more components of the plurality of components 321 are experiencing a failure. In an embodiment, the machine learning processors and/or deep learning neural networks learn to identify failures based on the operational data from the monitoring devices 322. In an embodiment, the machine learning processors use a Bayesian model technique to learn and determine failures based on the operational data. The deep learning neural networks can be, for example, convolutional neural networks, recurrent neural networks, feed forward neural networks, radial basis function neural networks, etc.

In an embodiment, the computer processors 317 generate user-executable instructions based, at least partially, on the historical information received from the remotely located database 330. For example, if information from call centers or similar remote medical devices indicate that a common failure of a particular component of the plurality of components 321 is that the particular component includes a certain defect (e.g., an air blockage in an air-line), the generated user-executable instructions can include instructions on how to remedy the certain defect.

In an embodiment, during execution of the AR application 316, the computer processors 317 carry out operations to cause the user interface 312 to display the information associated with the failing components of the plurality of components 321. In an embodiment, the computer processors 317 cause the user interface 312 to display the user-executable instructions in the form of a static image. The static image can include pictures, drawings, and/or text. For example, in an embodiment, the computer processors 317 cause the user interface 312 to display a series of pictures showing how to troubleshoot a blood pump of a dialysis machine. The series of pictures can be accompanied by supporting text to help the user understand how to troubleshoot the blood pump. In an embodiment, the computer processors 317 cause the user interface 312 to display the information in the form of an animated image. The animated image can include animated drawings, pre-recorded video, and/or text. For example, in an embodiment, the computer processors 317 cause the user interface 312 to display an animated drawing showing the steps of troubleshooting a dialyzer of a medical device 320. In an embodiment, the computer processors 317 cause the user interface 312 to display the information in the form of both static and animated images.

In an embodiment, during execution of the AR application 316, the computer processors 317 carry out operations to cause the user interface 312 to prompt a user to carry out the user-executable instructions included in the displayed information. As previously indicated, the user-executable instructions can include instructions on how to fix the failure of the failing components of the plurality of components 321. In an embodiment, the computer processors 317 prompt the user to confirm that the failing components of the plurality of components 321 are indeed experiencing a failure.

In an embodiment, the user-executable instructions include instructions on how to confirm that the failing components of the plurality of components 321 are indeed experiencing a failure. For example, if the failing components of the plurality of components 321 is a blood pump, the user-executable instructions can include instructions on how to confirm that a particular monitoring device of the plurality of monitoring devices 322 that is monitoring the blood pump (e.g., a pressure sensor) is connected and/or operating properly. If the particular monitoring device of the plurality of monitoring devices 322 is connected and/or operating properly, the user can confirm, using the user interface 312 for example, that the failing component of the plurality of components 321 is indeed experiencing failure. In an embodiment, upon confirming that the failing component of the plurality of components 321 is experiencing failure, the computer processors 317 cause the user interface 312 to display further user-executable instructions on how to fix the failure.

As indicated previously, the computer processors 317 can generate a confidence value associated with the determination that the failing component of the plurality of components 321 is indeed experiencing a failure. In an embodiment, before causing the user interface 312 to prompt the user to fix the failure, the computer processors 317 cause the user interface 312 to prompt the user to confirm that the failing components of the plurality of components 321 are indeed experiencing failure when the confidence value exceeds a first confidence value threshold but does not exceed a second confidence value threshold. For example, in an embodiment, if the generated confidence value exceeds 35% but does not exceed 75%, the computer processors 317 cause the user interface 312 to prompt the user to confirm the existence of the determined failures before causing the user interface 312 to prompt the user to fix the failure. In an embodiment, the computer processors 317 cause the user interface 312 to prompt the user to fix the failure without prompting the user to confirm the failure when the generated confidence value exceeds the second confidence value threshold (e.g., 75%). The first and second confidence value thresholds can be user selected or design choices based on, for example, accuracy, power efficiency, and safety considerations.

As indicated previously, the AR application 316 can include several modes. In an embodiment, each of the several modes can correspond to the user's experience level with the medical device 320. For example, the AR application 316 can include a novice mode and an expert mode. In an embodiment, while the AR application 316 is being executed, the computer processors 317 cause the user interface 312 to prompt the user to select a mode corresponding to the user's experience level. For instance, the user can select a novice mode if the user is a new patient or a new trainee. The user can select an expert mode if the user has significant experience using the medical device 320. In an embodiment, after the computer processors 317 determine that one or more components of the plurality of components 321 are experiencing a failure, the computer processors 317 initiate a real-time video conference with an expert technician based on the user confirmed experience level. In an embodiment, the computer processors 317 cause the user interface 312 to prompt the user to confirm that the user wants to initiate the real-time video conference with an expert technician. The choice to initiate the real-time video conference with an expert technician can occur only when the AR application 316 is being executed according to the user confirmed experience level or anytime a component of the plurality of components 321 is determined to be experiencing a failure. The decision to initiate a real-time video conference with an expert technician can also be at least partially based on the complexity of the one or more components of the plurality of components 321 determined to be experiencing a failure, or the seriousness of the failure. For example, in an embodiment, when the one or more components of the plurality of components determined to be experiencing a failure includes highly technical features, the expert technician video conference is initiated. In an embodiment, if the one or more failing components of the plurality of components 321 are experiencing a full failure, the expert technician video conference is initiated.

Figure 4A:
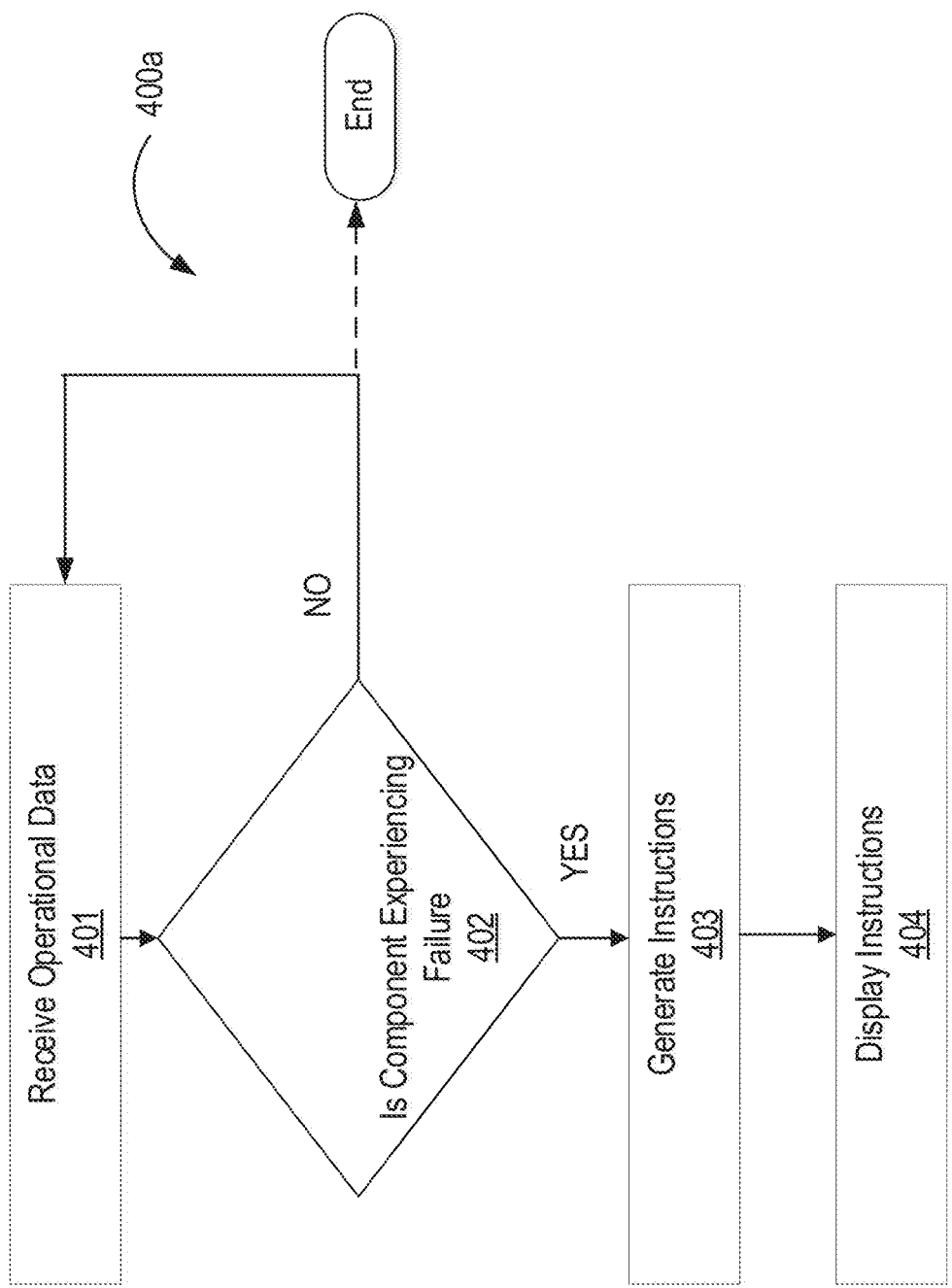
FIG. 4A shows a flowchart depicting an example of a method for providing augmented reality-based troubleshooting for medical devices, in accordance with one or more embodiments of the present disclosure.

FIG. 4A shows a flowchart depicting an example of a method 400a for providing augmented reality-based troubleshooting for medical devices, in accordance with one or more embodiments of the present disclosure. For illustrative purposes, the method 400a is shown as performed by the system 300 for providing augmented reality-based troubleshooting for medical devices, as previously described with reference to FIG. 3. The method 400a includes receiving operational data (block 401) and determining if a component is experiencing failure (block 402). If it is determined that a component is experiencing failure, the method 400a includes generating instructions (block 403) and displaying the instructions (block 404).

The method 400a includes receiving operational data (block 401). When the operating system 315 is executing the AR application 316, the computer processors 317 carry out operations to receive operational data associated with the operational parameters of the plurality of components 321 from the monitoring devices 322. For example, in an embodiment, the plurality of components 321 include one or more pumps and the computer processors 317 receive, from the monitoring devices 322, pressure data associated with fluid pressure levels (i.e., operational parameter) of the one or more pumps. In an embodiment, the plurality of components include a dialyzer and the computer processors 317 receive, from the monitoring device 322, blood detection data associated with an amount of blood (i.e. operational parameter) leaving a dialyzer. In an embodiment, the plurality of components 321 include one or more heating elements, and the computer processors 317 receive temperature data, from the monitoring devices 322, associated with operational temperatures (i.e. operational parameter) of the one or more heating elements.

The method 400a includes determining if a component is experiencing failure (block 402). During execution of the AR application 316, the computer processors 117 carry out operations to determine that one or more of the components of the plurality of components 321 are experiencing a failure based on the received operational data. The failure can be full or partial. For example, in an embodiment, if the operational data indicates that blood was detected downstream from a dialyzer of the medical device 320, the computer processors 317 determine that the dialyzer is experiencing a failure. In an embodiment, if the blood detection data indicates that more than a threshold amount of blood was detected (e.g., 5 ml, 10 ml, etc.), the computer processors 317 determine that the dialyzer is experiencing a full failure. In an embodiment, if the received operational data indicates that fluid flowing through the medical device 320 is below a threshold temperature, the computer processors 317 determine that one or more heating elements of the medical device 320 are experiencing failure.

If it is not determined that a component is experiencing failure, the method 400a includes either continuing to receive operational data (block 401) or ending operations. In an embodiment, the method 400a includes ending operations if it is not determined that a component of the plurality of components 321 is experiencing a failure during a predetermined time interval. For example, the operating system 315 can discontinue the execution of the AR application 316 if it is not determined that a component of the plurality of components 321 is experiencing failure during a one minute time interval (or thirty seconds, two minutes, three minutes, etc.). The time interval can be user selected or a manufacturing design choice based on desired power savings for the mobile device 310.

If it is determined that a component is experiencing failure, the method 400a includes generating instructions (block 403). During execution of the AR application 316, the computer processors 317 carry out operations to generate user-executable instructions if the computer processors 317 determine that one or more components of the plurality of components 321 are experiencing a failure (the "failing components"). The user-executable instructions correspond to the one or more failing components of the plurality of components 321. In an embodiment, the user-executable instructions include general troubleshooting instructions associated with the one or more failing components of the plurality of components 321. For example, in response to operational data indicating high return pressure (e.g., above a return pressure threshold) of a return pump in a dialysis circuit, the user-executable instructions can include instructions on how to perform general visual checks on each feature of the circuit.

In an embodiment, the user-executable instructions includes specific instructions associated with how to fix the one or more failing components of the plurality of components 321, based at least partially on the received operational data. For example, in response to operational data indicating high filter pressure associated with a filter of the medical device 320, the user-executable instructions can include, based on the magnitude of the indicated high filter pressure, one of: how to ensure the filter line is free from kinks (e.g., bends, curves, knots, etc.); how to ensure that the filter lines do not include clamps; and/or how to ensure that an appropriate fluid flow rate has been selected. In an embodiment, the computer processors 317 include machine learning processors and/or deep learning neural networks to facilitate the determining if the one or more components of the plurality of components 321 are experiencing a failure. In an embodiment, the machine learning processors and/or deep learning neural networks learn to identify failures based on the operational data from the monitoring devices 322. In an embodiment, the machine learning processors use a Bayesian model technique to learn and determine failures based on the operational data. The deep learning neural networks can be, for example, convolutional neural networks, recurrent neural networks, feed forward neural networks, radial basis function neural networks, etc.

If it is determined that a component is experiencing failure, the method 400a includes displaying instructions (block 404). During execution of the AR application 316, the computer processors 317 carry out operations to cause the user interface 312 to display the user-executable instructions associated with the one or more failing components of the plurality of components 321. In an embodiment, the computer processors 317 cause the user interface 312 to display the user-executable instructions in the form of a static image. The static image can include pictures, drawings, and/or text. For example, in an embodiment, the computer processors 317 cause the user interface 312 to display a series of pictures showing how to troubleshoot a blood pump of a dialysis machine. The series of pictures can be accompanied by supporting text to help the user understand how to troubleshoot the blood pump. In an embodiment, the computer processors 317 cause the user interface 312 to display the information in the form of an animated image. The animated image can include animated drawings, pre-recorded video, and/or text. For example, in an embodiment, the computer processors 317 cause the user interface 312 to display an animated drawing showing the steps of troubleshooting a dialyzer of a medical device 320. In an embodiment, the computer processors 317 cause the user interface 312 to display the information in the form of both static and animated images.

Figure 4B:
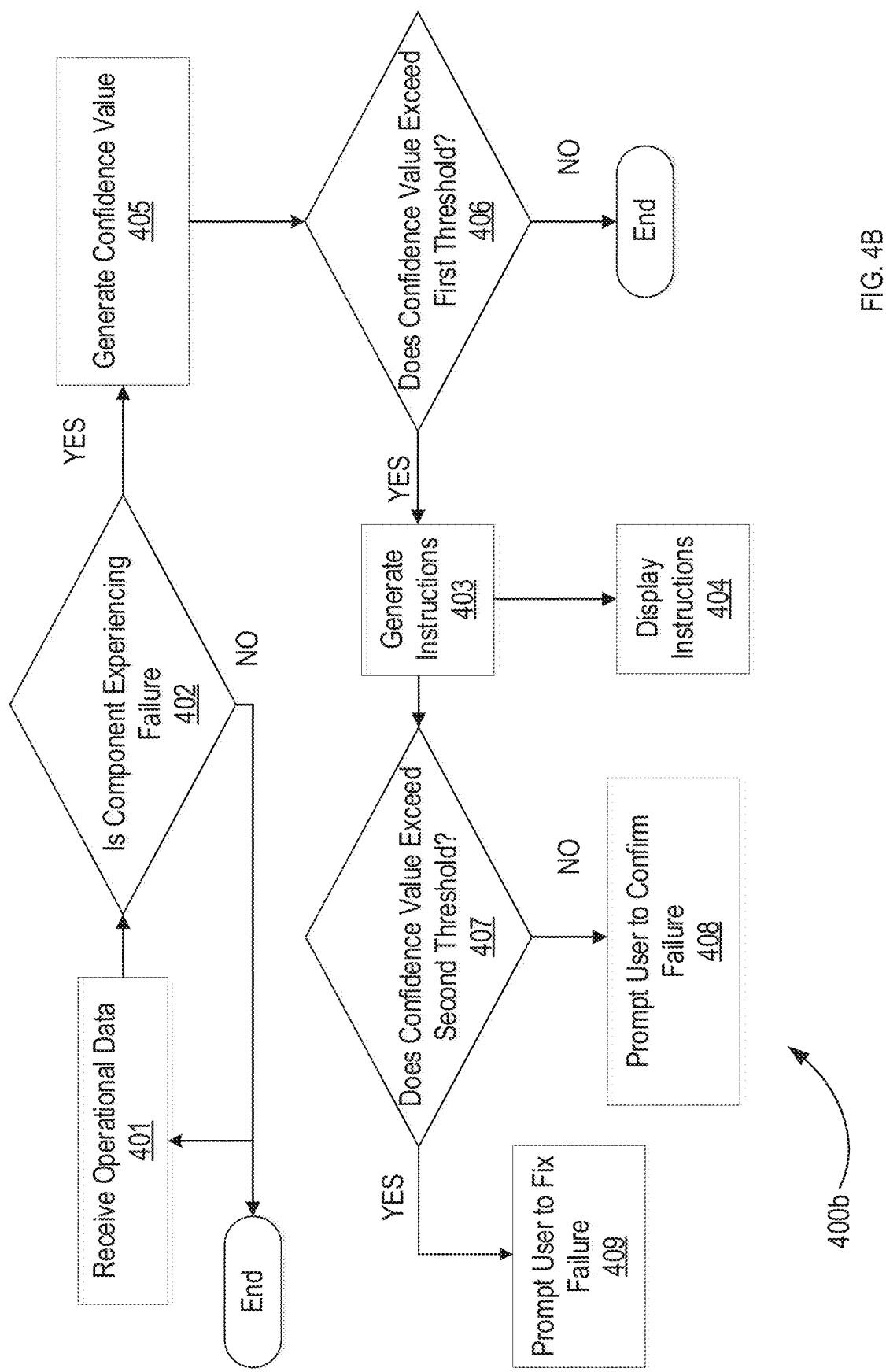
FIG. 4B shows a flowchart depicting an example of a method for providing confidence-driven augmented reality-based troubleshooting for medical devices, in accordance with one or more embodiments of the present disclosure.

FIG. 4B shows a flowchart depicting an example of a method 400b for providing confidence driven augmented reality-based troubleshooting for medical devices, in accordance with one or more embodiments of the present disclosure. For illustrative purposes, the method 400b is shown as performed by the system 300 for providing augmented reality-based troubleshooting for medical devices, as previously described with reference to FIG. 3. The method 400b includes receiving operational data (block 401) and determining if a component is experiencing failure (block 402) as previously described in the method 400a for providing augmented reality-based troubleshooting for medical devices with reference to FIG. 4A. If it is determined that a component is experiencing failure, the method 400b includes generating a confidence value (block 405) and determining if the confidence value exceeds a first threshold (block 406). If it is determined that the confidence interval exceeds a first threshold, the method 400b includes generating instructions (block 403), displaying instructions (block 404), and determining if the confidence values exceeds a second threshold (block 407). Blocks 403 and 404 are previously described in the method 400a for providing augmented reality-based troubleshooting for medical devices with reference to FIG. 4A. If it is determined that the confidence value does not exceed the second threshold, the method 400b includes prompting the user to confirm the failure (block 408). If it is determined that the confidence value exceeds the second threshold (e.g., the confidence interval is greater than or equal to the second threshold) the method 400b includes prompting the user to fix the failure (block 409).

The method 400b includes generating a confidence value (block 405). As previously indicated, during execution of the AR application 316, the computer processors 317 can carry out operations to determine if one or more components of the plurality of components 321 are experiencing a failure. If it is determined that one or more components of the plurality of components 321 are experiencing failure, the computer processors 317 generate a confidence value associated with the amount of certainty surrounding the determination that the one or more components of the plurality of components 321 are experiencing a failure. For example, the computer processors 317 can generate a value indicating that it is 60% likely that a particular component of the plurality of components 321 is indeed experiencing a failure, which can mean that it is more likely than not the particular component is experiencing a failure. The computer processors 317 can generate a value indicating that it is 90% likely that a particular component of the plurality of components 321 is experiencing a failure, which can mean that it is highly likely that the particular component is experiencing failure. The computer processors 317 can generate a value indicating that it is 25% likely that a particular component of the plurality of components 321 is experiencing failure, which can mean it is not likely that the particular component is actually experiencing a failure.

In an embodiment, the confidence value is based at least partially on the received operational data. For example, in an embodiment, if the operational data includes data indicating that a pump of the medical device 320 is experiencing a slight decrease in pressure from an optimal pressure value (e.g., desired pressure value based on safety considerations), the computer processors 317 generate a confidence value indicating that the pump is possibly experiencing a failure (e.g., the computer processors 317 are 35% sure that the pump is experiencing a failure.) In an embodiment, if the operational data includes data indicating that a pump of the medical device 320 is experiencing a large decrease in pressure from an optimal pressure value, the computer processors 317 generate a confidence value indicating that the pump is very likely experiencing a failure (e.g., the computer processors 317 are 90% sure that the pump is experiencing a failure).

The method 400b includes determining if the confidence value is above a first threshold (block 406). The computer processors 317 compare the confidence value generated in block 405 with a first confidence value threshold. The first confidence value threshold can be user selected or a design choice based on, for example, accuracy, safety, and efficiency considerations. In an embodiment, if the generated confidence value does not exceed the first threshold, the method 400b includes ending operations. For example, in an embodiment, the computer processors 317 carry out operations to stop execution of the AR application 316 if it is determined that none of the components of the plurality of components 321 are experiencing a failure with a confidence value exceeding the first confidence threshold value. In an embodiment, the computer processors 317 carry out operations to prompt the user to choose to stop execution of the AR application 316 if it is determined that none of the components of the plurality of components 321 are experiencing a failure with a confidence value exceeding the first confidence threshold value.

In an embodiment, if it is determined that the confidence value is above a first threshold, the method 400b includes generating instructions (block 403) and displaying instructions (block 404) as previously described in the method 400a for providing augmented reality-based troubleshooting for medical devices with reference to FIG. 4A.

If it is determined that the confidence value is above a first threshold, the method 400b also includes determining if the confidence interval is below a second threshold (block 407). The computer processors 317 compare the confidence value generated in block 405 with a second confidence value threshold. In an embodiment, the second confidence value threshold is larger than the first confidence value threshold. For example, the second confidence value threshold can be 90%, while the first confidence value threshold can be 60%. The second confidence value threshold can be user selected or a design choice based on, for example, accuracy, safety, and efficiency considerations.

If it is determined that the confidence value exceeds the second confidence value threshold, the method 400b includes prompting the user to fix the failure (block 409). As previously indicated, the user-executable instructions can include instructions on how to fix the failure of the one or more failing components (e.g., components determined to be experiencing a failure) of the plurality of components 321. The computer processors 317 carry out operations to cause the user interface 312 to prompt the user to fix the failure of the one or more failing components of the plurality of components 321 by following the user-executable instructions.

If it is determined that the confidence value does not exceed the second confidence value threshold, the method 400b includes prompting the user to confirm the failure (block 408). As previously indicated with reference to FIG. 3, the user-executable instructions can include instructions on how to confirm that the one or more failing components of the plurality of components 321 is indeed experiencing a failure. The computer processors 317 prompt the user to confirm the failure of the one or more failing components of the plurality of components 321 by carrying out the user-executable instructions. For example, if the one or more failing components of the plurality of components 321 includes a blood pump, the user-executable instructions can include instructions on how to confirm that the monitoring device 322 monitoring the blood pump (e.g., a pressure sensor) is connected and operating properly. If the monitoring device 322 is connected and operating properly, the user can confirm, using the user interface 312 for example, that the failing component is indeed experiencing a failure. In an embodiment, upon confirming that the failing component is experiencing a failure, the computer processors 317 cause the user interface 312 to display further user-executable instructions on how to fix the failure.

FIG. 4C shows a flowchart depicting an example of a method 400c for providing virtual assistance for augmented reality-based troubleshooting for medical devices, in accordance with one or more embodiments of the present disclosure. For illustrative purposes, the method 400c is shown as performed by the system 300 for providing augmented reality-based troubleshooting for medical devices, as previously described with reference to FIG. 3. The method 400c for providing virtual assistance for augmented reality-based troubleshooting for medical devices can be used along with methods for providing reality-based troubleshooting for medical devices. For example, in an embodiment, the method 400c is used with the method 400a for providing augmented reality-based troubleshooting for medical devices previously described with reference to FIG. 4A.

In an embodiment, the method 400c is used with the method 400b for providing confidence driven augmented reality-based troubleshooting for medical devices previously described with reference to FIG. 4B. The method 400c includes receiving operational data (block 401) and determining if a component is experiencing failure (block 402). Blocks 401 and 402 are previously described in the method 400a for providing augmented reality-based troubleshooting for medical devices with reference to FIG. 4A. If it is determined that a component is experiencing failure, the method 400c includes determining if the user is a novice (block 410). If it is determined that the user is a novice, the method 400c includes initiating virtual assistant (block 411). If it is determined that the user is not a novice, the method 400c includes generating instructions (block 403) and displaying instructions (block 404). Blocks 403 and 404 are previously described in the method 400a for providing augmented reality-based troubleshooting for medical devices with reference to FIG. 4A.

The method 400c includes determining if a user is a novice (block 410). In an embodiment, during execution of the AR application 316, the computer processors 317 carry out operations to determine if the user is a novice. As indicated previously, the AR application 316 can include several modes. In an embodiment, each of the several modes can correspond to the user's experience level with the medical device 320. For example, the AR application 316 can include a novice mode and an expert mode. In an embodiment, while the AR application 316 is being executed, the computer processors 317 cause the user interface 312 prompt the user to select a mode corresponding to the user's experience level. For instance, the user can select a novice mode if the user is a new patient or a new trainee. The user can select an expert mode if the user has significant experience using the medical device 320. Based on the user's selection, the computer processors 317 can determine if the user is a novice user or an experienced user of the medical device 320. In an embodiment, historical data received from the remotely located database 330 is used to determine the user's experience level. For example, the remotely located database 330 can store information associated with previous set-up and maintenance attempts by the user. The computer processors 317 can use this information to determine, for example, a number of successful setups (e.g., set-up attempts with little to no mistakes) or the number of times a user has performed a specific troubleshooting/maintenance on a particular component. Based on this determination, the computer processors 317 can determine if the user is, for example, a novice user or an experienced user.

If it is determined that the user is experienced, the method 400c includes generating instructions (block 403) and displaying instructions (block 404) as previously described in the method 400a for providing augmented reality-based troubleshooting for medical devices with reference to FIG. 4A.

If it is determined that the user is a novice, the method includes initiating virtual assistant (block 411). In an embodiment, after the computer processors 317 determine that one or more components of the plurality of components 321 are experiencing a failure, the computer processors 317 initiate a real-time video conference with an expert technician based on the user confirmed experience level. In an embodiment, the computer processors 317 cause the user interface 312 to prompt the user to confirm that the user wants to initiate the real-time video conference with an expert technician. The choice to initiate the real-time video conference with an expert technician can occur only when the AR application 316 is being executed according to the user confirmed experience level. However, in an embodiment, the choice to initiate the real-time video conference with an expert technician occurs anytime a component 321 is determined to be experiencing a failure. The decision to initiate a real-time video conference with an expert technician can also be at least partially based on the complexity of the one or more components of the plurality of components 321 determined to be experiencing a failure, or the seriousness of the failure. For example, in an embodiment, when a failing component of the plurality of components 321 includes highly technical features, the expert technician video conference is initiated. In an embodiment, if the failing component is experiencing a full failure the real-time expert technician video conference is initiated.

Figure 5:
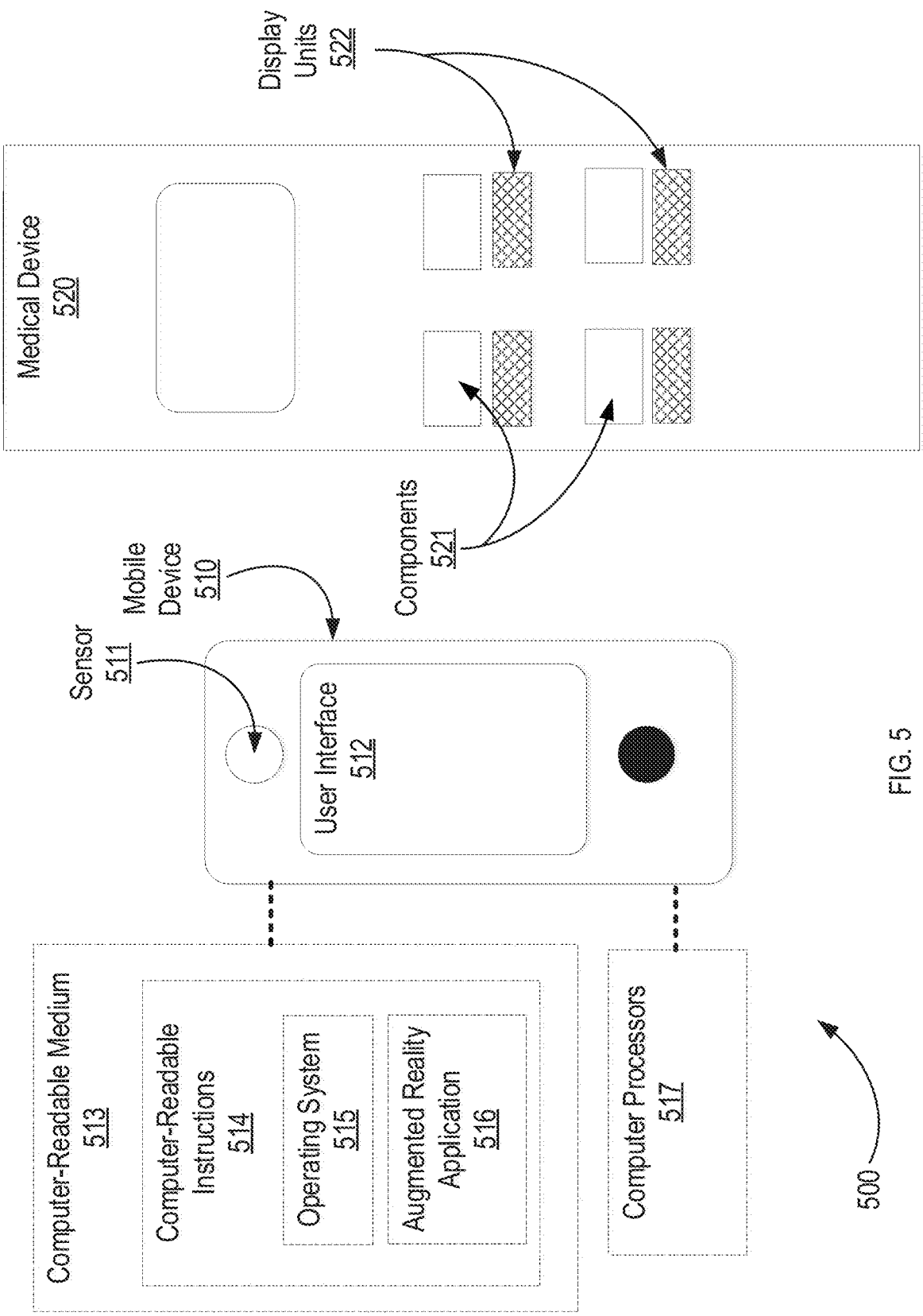
FIG. 5 shows an example of a system for providing augmented-reality based diagnostics for medical devices, in accordance with one or more embodiments of the present disclosure.

FIG. 5 shows an example of a system 500 for providing augmented-reality based diagnostics for medical devices, in accordance with one or more embodiments of the present disclosure. The system 500 includes a mobile device 510 and a medical device 520. The mobile device 510 includes a sensor 511 and a user interface 512. The mobile device 510 also includes a computer-readable medium 513 and computer processors 517. The computer-readable medium 513 includes computer-executable instructions 514. The computer-executable instructions 514 include an operating system 515 and an augmented reality (AR) application 516. The medical device 520 includes a plurality components 521, and a plurality of display units 522.

The medical device 520 is configured to perform medical functions. As used herein, medical functions refer to one or more of: (1) the diagnosis, prevention, monitoring, treatment, and/or alleviation of disease; (2) the diagnosis, monitoring, treatment, alleviation, or compensation for an injury or handicap; or (3) the investigation, replacement, and/or modification of the anatomy and/or a physiological process. For illustrative purposes, the medical devices 120 in the shown embodiment is a dialysis machine configured to provide dialysis treatment, such as hemodialysis or peritoneal dialysis, and/or other renal replacement therapy, such as hemofiltration or hemodiafiltration.

The medical device 520 includes a plurality of components 521 that work together to allow the medical device 520 to perform medical functions. For example, in the shown embodiment, the plurality of components 521 of the medical device 520 include several dialysis machine components. The dialysis machine components can include, for example, dialyzers, blood pumps, deaeration tanks, blood pressure cuffs, monitors, brakes, shunt interlocks, pressure gauges, flowmeters, dialysate pumps, clamps, etc.

Each display unit of the plurality of display units 522 are associated with the components 521 of the medical device 520. In the shown embodiment, the plurality of display units 522 include at least one light emitting diode (LED) display. In an embodiment, the plurality of display units include at least one liquid crystal display (LCD). In an embodiment each display unit of the plurality of display units 522 is configured to display characters (e.g., alphanumeric text) that correspond to one or more operating parameters of a component of the plurality of components 521. For example, in an embodiment, the plurality of components 521 include a dialysate pump and at least one display unit of the plurality of display units 522 displays numerical values associated with the measured pressure (i.e., operating parameter) of the dialysate pump. In an embodiment, the plurality of components 521 include a venous line and at least one display unit of the plurality of display units 522 displays numerical values associated with the measured pressure (i.e., operating parameter) of the venous line. In an embodiment, one or more display units of the plurality of display units 522 include visual tags (e.g., IR tags, barcodes, etc.) associated with the component of the plurality of components 521 that is associated with each display unit of the plurality of display units. For example, if a particular display unit of the plurality of display units 522 corresponds with a dialyzer, the particular display unit can include visual tags corresponding to the dialyzer.

The mobile device 510 can be one of several types of mobile devices. For example, in the illustrated embodiment, the mobile device 510 is a cellular phone (e.g., smart phone). In an embodiment, the mobile device 510 is a tablet personal computer (PC). The mobile device 510 can also be a wireless wearable interface device, such as a wrist-worn display and/or a head-mounted display. The mobile device 510 is configured to provide various functionalities. For example, in an embodiment, the mobile device 510 is configured to provide voice calls and text messaging. In an embodiment, the mobile device 510 is configured to display photographs and/or videos. In an embodiment, the mobile device 510 is configured to play music and other forms of audio. The mobile device 510 can also be configured to send and receive e-mails, capture and display photographs, capture and display videos, access websites, and display websites.

In an embodiment, the sensor 511 is configured to capture image data. In an embodiment, the sensor 511 is a camera. The camera can capture image data in the form of still images and/or video. The image data can take the form of several image data formats, such as RAW, JPEG, PNG, etc. In an embodiment, the sensor 511 is a digital camera that uses a charged-coupled device (CCD) and/or complementary metal oxide semiconductor (CMOS) to convert photons to electrons for digital processing. In an embodiment, the sensor 511 is a laser scanner. The sensor 511 can also be an LED scanner, an imaging scanner, and/or a radio frequency identification (RFID) scanner. Although the mobile device 510 is shown with only one sensor 511, the mobile device 510 can include several sensors 511 of several types. For example, in an embodiment, the mobile device 510 includes sensors 511 that are a camera and a laser scanner. In an embodiment, the sensor 511 is configured to detect the displayed characters of at least one of the displays in the plurality of displays 522.

In an embodiment, the user interface 512 is a graphical user interface (GUI). The user interface 512 is configured to allow a user of the mobile device 110 to interact with the mobile device 510 through graphical icons and visual indicators. The user interface 512 can use a windows, icons, menus, pointer paradigm (WIMP) to allow a user to interact with the mobile device 510. In an embodiment, the user interface 512 is a touchscreen GUI. The user interface 512 can also use a post-WIMP paradigm typically found in touchscreen-based GUIs. The user interface 512 is configured to display images in the form of still photographs and/or videos.

The computer-readable medium 513 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In an embodiment, the computer-readable medium 513 includes code-segment having executable instructions. In an embodiment, the computer-readable medium 513 stores information corresponding to the components 521 of the medical device 520. The information includes setup, maintenance, and/or troubleshooting instructions (i.e., user-executable instructions) associated with the components 521 of the medical device 520. For example, in an embodiment, the medical device 520 includes a dialyzer (i.e., component 521) and the information includes user-executable instructions on how to setup a dialyzer within a holding chamber of the medical device 520. In an embodiment, the medical device 520 includes arterial lines and the information includes user-executable instructions on how to perform maintenance on arterial lines. In an embodiment, the medical device 520 includes a blood pump and the information includes user-executable instructions on how to troubleshoot the blood pump.

The computer processors 517 are communicatively coupled to the sensor 511. In an embodiment, the computer processors 517 include a general purpose processor. In an embodiment, the computer processors 517 include a central processing unit (CPU). In an embodiment, the computer processors 517 include at least one application specific integrated circuit (ASIC). The computer processors 517 can also include general purpose programmable microprocessors, special-purpose programmable microprocessors, digital signal processors (DSPs), programmable logic arrays (PLAs), field programmable gate arrays (FPGA), special-purpose electronic circuits, etc., or a combination thereof. The computer processors 517 are configured to execute program code means such as the computer-executable instructions 5114. In an embodiment, the computer processors 517 include neural network processors. The neural network processors can perform a variety of machine learning algorithms, such as deep learning techniques (e.g., convolutional, radial basis function, recurrent, and/or modular neural network processing techniques) and/or Bayesian learning techniques.

The operating system 515 is configured to execute the AR application 516. In an embodiment, the operating system 515 is configured to execute the AR application 516. In an embodiment, the operating system 515 is configured to execute the AR application 516 upon the occurrence of a user initiated command. A user can, for example, command the operating system 515 to begin executing the AR application 516 by clicking and/or touching an icon representing the AR application 516 on the user interface 512. The operating system 515 can execute the AR application 516 in a foreground state and/or a background state. The AR application 516 can include one or more modes of operation. For example, in an embodiment, the AR application 516 includes a novice mode. In an embodiment, the AR application 516 includes an expert mode.

When the operating system 515 is executing the AR application 516, the computer processors 517 carry out one or more operations. In an embodiment, when the operating system 515 is executing the AR application 516, the computer processors 517 carry out operations to cause the sensor 511 to begin detecting the numerical values displayed by the plurality of display units 522. To facilitate the detecting of the displayed numerical values, the computer processors 517 can carry out operations to cause the user interface 512 to display a message to a user prompting the user to point the sensor 511 towards at least one display unit of the plurality of display units 522. As previously indicated, each display unit of the plurality of display units 522 can include visual tags associated with a component of the plurality of components 521 that is associated with a particular display unit. In an embodiment, the sensor 511 captures these visual tags such that the detected numerical values are associated with the components to which they correspond. In an embodiment, the sensor 511 is configured to detect changes of the numerical values.

In an embodiment, when the operating system 515 is executing the AR application 516, the computer processors 517 carry out operations to cause the user interface 512 to display an illustrative representation associated with the numerical values of at least one display unit of the plurality of display units 522. In an embodiment, the computer processors 517 are configured to use OCR techniques to recognize the detected displayed numbers. In an embodiment, the illustrative representation is a dial display that illustrates the detected numerical values of at least one display unit of the plurality of display units 522. In an embodiment, the illustrative representation is a meter display that illustrates the numerical values detected of at least one display unit of the plurality of display units 522. In an embodiment, the user interface 512 displays the same illustrative representations for every component of the plurality of components (e.g., each component corresponds to a dial display or each component corresponds to a meter display). In an embodiment, the user interface 512 displays some illustrative representations for some components and other illustrative representations for some components (e.g., some components have a meter display and some components have dial displays). The types of illustrative representations can be selected by the user or implemented as a manufacturer design choice, and can be based on the type of component and/or operational parameter associated with the display units of the plurality of display units 522.

In an embodiment, when the operating system 515 is executing the AR application 516, the computer processors 517 carry out operations to generate a graph representing trend data associated with the detected numerical values of at least one display unit of the plurality of display units 522. In an embodiment, the graph is generated in real-time. For example, in an embodiment, the plurality of components 521 include a venous line and the detected numbers correspond to the amount of pressure measured (i.e. operating parameter) at a given time for the venous line. Over time, the measured pressure can change for the venous line. The computer processors 517 carry out operations to generate a graph that shows the detected numbers of the venous line over time, and thus the change in pressure over time (i.e., trend data) can be mapped. In an embodiment, the computer processors 517 cause the user interface 512 to display the generated graph.

In an embodiment, during execution of the AR application 516, the computer processors 517 carry out operations to compare the trend data against threshold values and determine if the component of the plurality of components 521 corresponding to the trend data is experiencing an at least partial failure. For example, the venous line can have a desired threshold pressure value that is optimized for efficient and safe blood return delivery to the patient during a dialysis operation. In an embodiment, if the generated graph shows that the pressure value for the venous line dips below the threshold value, the computer processors 517 determines that the venous line is experiencing a failure. The failure can be partial or complete. For example, a slight dip below the threshold value may indicate that the venous line is experiencing a partial failure but is still operational. Thus, a dialysis treatment may can be completed and the venous line can be fixed after the dialysis treatment. However, if for example, the graph shows a large dip below the threshold value, it may indicate that the current dialysis treatment is unsafe and should be stopped immediately. As another example, if the pressure value for the venous line dips below the threshold value for a threshold period of time, it can indicate a partial or full failure.

In an embodiment, when it is determined that a component is experiencing a failure, the computer processors 517 are configured to generate an alert to inform the user that a component is experiencing a failure. In an embodiment, the alert is a visual alert displayed by the user interface 512. In an embodiment, the alert includes the computer processors 517 causing the mobile device 510 to vibrate or make an audible sound.

Figure 6:
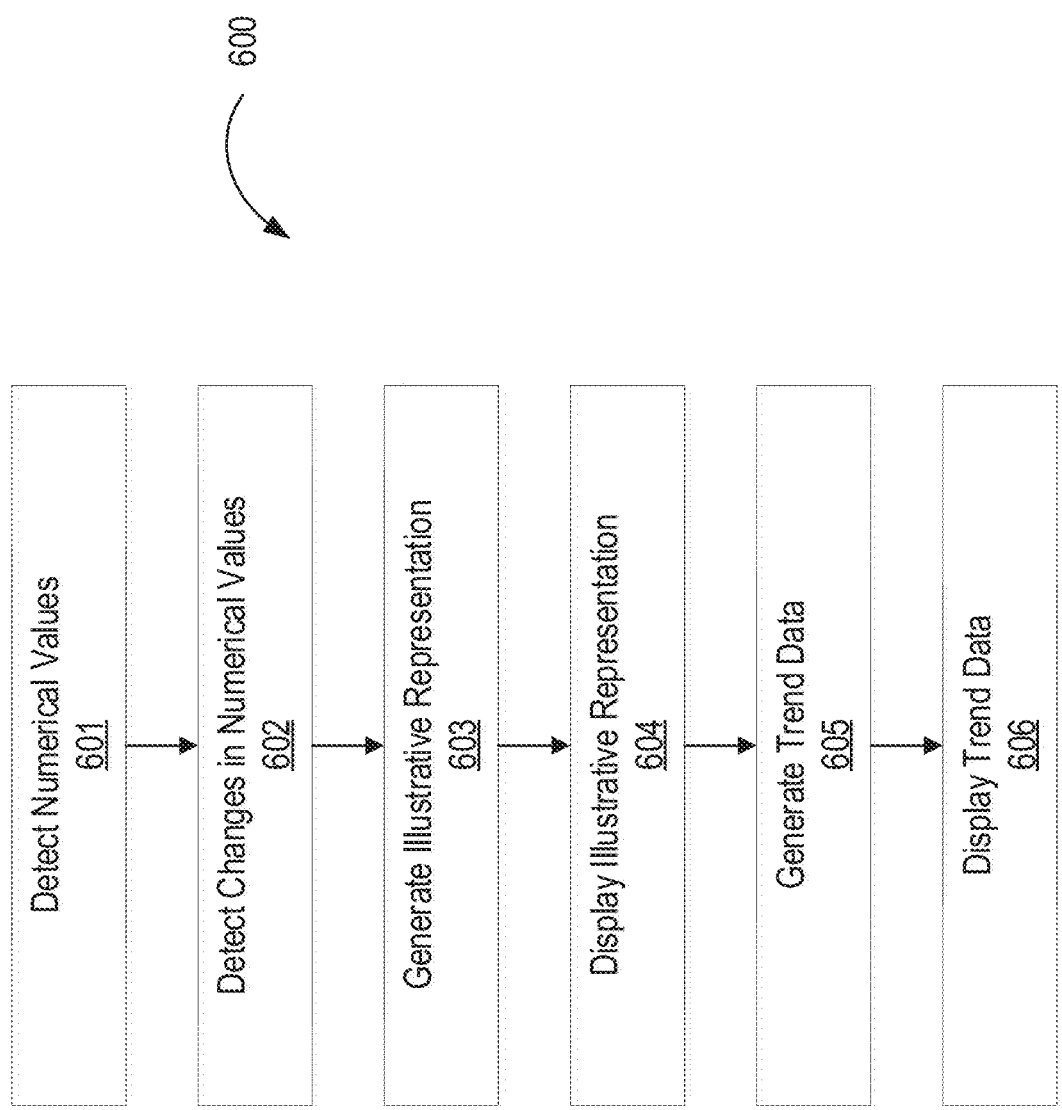
FIG. 6 shows a flowchart depicting an example of a method for providing augmented-reality based diagnostics for medical devices, in accordance with one or more embodiments of the present disclosure.

FIG. 6 shows a flowchart depicting an example of a method 600 for providing augmented-reality based diagnostics for medical devices, in accordance with one or more embodiments of the present disclosure. The method 600 includes detecting numerical values (block 601), detecting changes in numerical values (block 602), generating illustrative representation (block 603), displaying illustrative representation (block 604), generating trend data (block 605) and displaying trend data (block 606).

The method 600 includes detecting numerical values (block 601). When the operating system 515 is executing the AR application 516, the computer processors 517 carry out operations to cause the sensor 511 to begin detecting the numerical values displayed by the plurality of display units 522. To facilitate the detecting of the displayed numerical values, the computer processors 517 can carry out operations to cause the user interface 512 to display a message to a user prompting the user to point the sensor 511 towards at least one display unit of the plurality of display units 522. As previously indicated, each display unit of the plurality of display units 522 can include visual tags associated with a component of the plurality of components 521 that is associated with a particular display unit. In an embodiment, the sensor 511 captures these visual tags such that the detected numerical values are associated with the components to which they correspond. In an embodiment, the sensor 511 is configured to detect changes of the numerical values.

The method 600 includes detecting changes in numerical values (block 602). As previously indicated, the operating parameters of each component of the plurality of components 521 can change overtime. Thus, the corresponding displayed numerical values will change over time. In an embodiment, when the operating system 515 is executing the AR application 516, the computer processors 517 carry out operations to cause the sensor 511 to continue detecting the numerical values displayed by the plurality of display units 522. Thus, the sensor 511 is configured to detect changes of the numerical values over time.

The method 600 includes generating an illustrative representation (block 603). When the operating system 515 is executing the AR application 516, the computer processors 517 carry out operations to generate, for at least one component of the plurality of components 521, an illustrative representation based on the detected numerical values of the corresponding display units of the plurality of display units 522. The illustrative representation can be a dial display and/or a meter display. For example, if the plurality of components 521 include a venous line, a meter and/or dial display can be generated based on the detected numerical values associated with the measured pressure of the venous line.

The method 600 includes displaying the illustrative representation (block 604). When the operating system 515 is executing the AR application 516, the computer processors 517 carry out operations to cause the user interface 512 to display an illustrative representation associated with the numerical values of at least one display unit of the plurality of display units 522. In an embodiment, the computer processors 517 are configured to use OCR techniques to recognize the detected displayed numbers. In an embodiment, the user interface 512 displays the same illustrative representations for every component of the plurality of components (e.g., each component corresponds to a dial display or each component corresponds to a meter display). In an embodiment, the user interface 512 displays some illustrative representations for some components and other illustrative representations for some components (e.g., some components have a meter display and some components have dial displays). The types of illustrative representations can be selected by the user or implemented as a manufacturer design choice, and can be based on the type of component and/or operational parameter associated with the display units of the plurality of display units 522.

The method 600 includes generating trend data (block 605). In an embodiment, when the operating system 515 is executing the AR application 516, the computer processors 517 carry out operations to generate a graph representing trend data associated with the detected numerical values of at least one display unit of the plurality of display units 522. In an embodiment, the graph is generated in real-time. For example, in an embodiment, the plurality of components 521 include a venous line and the detected numbers correspond to the amount of pressure measured (i.e. operating parameter) at a given time for the venous line. Over time, the measured pressure can change for the venous line. The computer processors 517 carry out operations to generate a graph that shows the detected numbers of the venous line over time, and thus the change in pressure over time (i.e., trend data) can be mapped.

In an embodiment, the computer processors 517 carry out operations to compare the trend data against threshold values and determine if the component of the plurality of components 521 corresponding to the trend data is experiencing an at least partial failure. For example, the venous line can have a desired threshold pressure value that is optimized for efficient and safe blood return delivery to the patient during a dialysis operation. In an embodiment, if the generated graph shows that the pressure value for the venous line dips below the threshold value, the computer processors 517 determines that the venous line is experiencing a failure. The failure can be partial or complete. For example, a slight dip below the threshold value may indicate that the venous line is experiencing a partial failure but is still operational. Thus, a dialysis treatment may can be completed and the venous line can be fixed after the dialysis treatment. However, if for example, the graph shows a large dip below the threshold value, it may indicate that the current dialysis treatment is unsafe and should be stopped immediately. As another example, if the pressure value for the venous line dips below the threshold value for a threshold period of time, it can indicate a partial or full failure.

The method 600 includes displaying trend data (block 606). In an embodiment, the computer processors 517 cause the user interface 512 to display the generated graph. In embodiments that include comparing the trend data against threshold value to determine if a component is experiencing a failure, the user interface 512 can also be caused to display an alert to inform the user that a component is experiencing a failure.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A system comprising:
a medical device comprising:
one or more components, each component of the one or more components having one or more operational parameters; and
one or more monitoring devices configured to detect the one or more operational parameters of at least one component of the one or more components;
an electronic mobile device, the electronic mobile device comprising:
a computer-readable medium comprising computer-executable instructions, the computer-executable instructions comprising:
an operating system; and
an augmented reality application configured to be executed by the operating system;
one or more processors configured to:
execute the computer-executable instructions,
be communicatively coupled to the one or more monitoring devices, and
receive operational data associated with the one or more operational parameters of the at least one component;
a user interface communicatively coupled to the one or more processors; and
wherein, when the operating system is executing the augmented reality application, the one or more processors carry out operations to:
receive the operational data associated with the one or more operational parameters of the at least one component;
determine if the at least one component is experiencing an at least partial failure based on the operational data;
generate one or more user-executable instructions based on the determining if the at least one component is experiencing an at least partial failure;
cause the user interface to display the user-executable instructions;
generate a confidence value for the determination that the at least one component is experiencing the at least partial failure;
cause the user interface to prompt the user to confirm the at least partial failure if the confidence value is greater than a first confidence value threshold and lesser than a second confidence value threshold; and
cause the user interface to prompt the user to fix the at least partial failure if the confidence value is greater than the second confidence value threshold.

2. The system of claim 1, wherein the user-executable instructions comprise information on how to confirm that the at least one component is experiencing the at least partial failure.

3. The system of claim 1, wherein the user-executable instructions comprise information relating to how to fix the at least partial failure.

4. The system of claim 1, wherein the one or more processors comprises at least one machine learning algorithm that determines if the at least one component is experiencing the at least partial failure and generates the one or more user-executable instructions.

5. The system of claim 1, wherein the electronic mobile device is configured to initiate a real-time video conference with an expert technician based on the magnitude of the at least partial failure.

6. The system of claim 1, wherein when the operating system is executing the augmented reality application, the one or more processors further carry out operations to prompt the user to confirm one of a plurality of user experience levels and the electronic mobile device is configured to initiate a real-time video conference with an expert technician based on the user-confirmed user experience level.

7. The system of claim 1, further comprising a remotely located database configured to store historical data associated with at least one of: the medical device or at least one remote device that is substantially similar to the medical device, wherein when the operating system is executing the augmented reality application, the one or more processors further carry out operations to receive the historical data, and wherein determining if the at least one component is experiencing an at least partial failure based at least partially on the received historical data.

8. The system of claim 1, further comprising a remotely located database configured to store historical data associated with at least one of: the medical device or at least one remote device that is substantially similar to the medical device, wherein when the operating system is executing the augmented reality application, the one or more processors further carry out operations to receive the historical data, and wherein generating the one or more user-executable instructions is at least partially based on the received historical data.

9. A method, comprising:
receiving, by one or more processors, operational data associated with one or more operational parameters of at least one component of a medical device,
determining, by the one or more processors, if the at least one component is experiencing an at least partial failure based on the operational data, generating, by one or more processors, one or more user-executable instructions based on the determining if the at least one component is experiencing an at least partial failure, causing, by the one or more processors, a user interface to display the one or more user-executable instructions;

generating a confidence value for the determination that the at least one component is experiencing an at least partial failure;

prompting a user to confirm the at least partial failure if the confidence value is greater than a first confidence value threshold and below a second confidence value threshold; and prompting the user to fix the at least partial failure if the confidence value is greater than the second confidence value threshold.

10. The method of claim 9, wherein the user-executable instructions comprise information on how to confirm that the at least one component is experiencing the at least partial failure.

11. The method of claim 9, wherein the user-executable instructions comprise information relating to how to fix the at least partial failure.

12. The method of claim 9, further comprising initiating a real-time video conference with an expert technician based on the magnitude of the at least partial failure.

13. The method of claim 9, further comprising prompting a patient to confirm one of a plurality of user experience levels initiating a real-time video conference with an expert technician based on the user-confirmed user experience level.

14. A system comprising:
a medical device comprising:
one or more components, each component of the one or more components having one or more operational parameters;
one or more monitoring devices configured to detect the one or more operational parameters of at least one component of the one or more components; and
one or more displays configured to display one or more numerical values associated with the one or more operational parameters of at least one component of the one or more components;
an electronic mobile device, the electronic mobile device comprising:
a computer-readable medium comprising computer-executable instructions, the computer-executable instructions comprising:
an operating system; and
an augmented reality application configured to be executed by the operating system;
one or more processors configured to:
execute the computer-executable instructions;
be communicatively coupled to the one or more monitoring devices, and
receive operational data associated with the one or more operational parameters of the at least one component;
a user interface communicatively coupled to the one or more processors;
one or more sensors configured to be communicatively coupled to the one or more processors and further configured to capture image data; and
wherein, when the operating system is executing the augmented reality application, the one or more processors carry out operations to:
cause the one or more sensors to begin detecting the one or more numerical values associated with one or more operational parameters, wherein the one or more sensors are configured to further detect changes associated with the one or more numerical values;
cause the user interface to display an illustrative representation associated with the detected one or more numerical values;
receive the operational data associated with the one or more operational parameters of the at least one component;
determine if the at least one component is experiencing an at least partial failure based on the operational data;
generate one or more user-executable instructions based on the determining if the at least one component is experiencing an at least partial failure;
cause the user interface to display the user-executable instructions;
generate a confidence value for the determination that the at least one component is experiencing the at least partial failure;
cause the user interface to prompt the user to confirm the at least partial failure if the confidence value is greater than a first confidence value threshold and lesser than a second confidence value threshold; and
cause the user interface to prompt the user to fix the at least partial failure if the confidence value is greater than the second confidence value threshold.

15. The system of claim 14, wherein the one or more displays comprise one or more LED displays.

16. The system of claim 14, wherein the illustrative representation comprises a dial display.

17. The system of claim 14, wherein the illustrative representation comprises a meter display.

18. The system of claim 14, wherein when the operating system is executing the augmented reality application, the one or more processors further carry out operations to generate a graph in real time, the graph representing trend data associated with the detected one or more numerical values.

19. The system of claim 18, wherein when the operating system is executing the augmented reality application, the one or more processors further carry out operations to compare the trend data against threshold values to determine if the at least one component is experiencing the at least partial failure.

20. The system of claim 19, wherein when the operating system is executing the augmented reality application, the one or more processors further carry out operations to alert a patient when it is determined that at least one component is experiencing the at least partial failure.

21. The system of claim 20, wherein the alert comprises the one or more processors causing the electronic mobile device to at least one of vibrate or generate an audible sound.

* * * * *